United States Patent
Malek et al.

(10) Patent No.: US 7,435,591 B2
(45) Date of Patent: Oct. 14, 2008

(54) COMPOSITIONS AND METHODS FOR INCREASING ANIMAL SIZE GROWTH RATE

(75) Inventors: Nisar P. Malek, Hanover (DE); James M. Roberts, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 128 days.

(21) Appl. No.: 10/502,001

(22) PCT Filed: Jan. 27, 2003

(86) PCT No.: PCT/US03/02423

§ 371 (c)(1),
(2), (4) Date: Jul. 19, 2004

(87) PCT Pub. No.: WO03/063581

PCT Pub. Date: Aug. 7, 2003

(65) Prior Publication Data

US 2005/0223417 A1     Oct. 6, 2005

Related U.S. Application Data

(60) Provisional application No. 60/352,391, filed on Jan. 28, 2002.

(51) Int. Cl.
| | |
|---|---|
| C12N 5/06 | (2006.01) |
| C12N 5/10 | (2006.01) |
| C12N 5/00 | (2006.01) |
| C12N 5/02 | (2006.01) |
| C12N 15/00 | (2006.01) |
| C12N 15/87 | (2006.01) |

(52) U.S. Cl. .................. 435/354; 435/375; 435/455; 435/320.1; 435/463

(58) Field of Classification Search .............. 435/354, 435/375, 455, 320.1, 463
See application file for complete search history.

(56) References Cited

U.S. PATENT DOCUMENTS

| 5,958,769 A | 9/1999 | Roberts et al. |
| 6,242,575 B1 | 6/2001 | Massague et al. |

OTHER PUBLICATIONS

Campbell and Wilmut, 1997, Totipotency or multipotency of cultured cells: applications and progress, Theriogenology, vol. 47, pp. 63-72.*
Wheeler, M.B. 2001, Transgenic technology and applications in swine. Theriogenology, vol. 56, pp. 1345-1369.*
Prelle, K. 1999, Establishment of pluripotent cell lines from verterbrate species-present status and future prosopects, Cells Tissues Organs, vol. 165, pp. 220-236.*
Thomson AJ et al., 2003, Gene targeting in livestock, Reprod. Supp., 61:495-508.*
Poljaeva, I.A., 2000, Clone pigs produced by nuclear transfer from adult somatic cells. Nature, 407:86-90.*
Williams, SH et al., 2003, Evaluation of gene targeting by homologous recombination in ovine somatic cells, Molecular Reproduction and Development, 66:115-125.*
Harrison, SJ et al., 2002, Efficient generation of a(1,3) galactosyltransferase knockout porcine fetal fibroblasts for nuclear transfer, Transgenic Research, 11:143-150.*
Denning, C et al., 2001, Gene targeting in primary fetal fibroblasts from sheep and pig, Cloning and Stem cells, 3:221-231.*
McCreath, 2000, Production of gene-targeted sheep by nuclear transfer from cultured somatic cells, Nature, vol. 405, pp. 1066-1069.*
Mir, B and Piedrahita, JA, 2004, Nuclear localization signal and cell synchrony enhance gene targeting efficiency in primary fetal fibroblasts, Nucl. Acids, Res., 32:e25.*
MSN Encarta dictionary definition of murine, printout dated Aug. 9, 2007, http://encarta.msn.com/encnet/features/dictionary/DictionaryResults.aspx?refid=1861631945.*
Agrawal, D. et al., "Repression of $p27^{kip1}$ synthesis by platelet-derived growth factor in BALB/c 3T3 cells," *Mol. Cell. Biol.*, 16(8):4327-4336 (Aug. 1996).
Bai, C. et al., "SKP1 connects cell cycle regulators to the ubiquitin proteolysis machinery through a novel motif, the F-box," *Cell*, 86(2):263-274 (Jul. 26, 1996).
Carrano, A. et al., "SKP2 is required for ubiquitin-mediated degradation of the CDK inhibitor p27," *Nat. Cell. Biol.*, 1(4):193-199 (Aug. 1999).
Feldman, R.M. et al., "A complex of Cdc4p, Skp1p, and Cdc53p/cullin catalyzes ubiquitination of the phosphorylated CDK inhibitor Sic1p," *Cell*, 91(2):221-230 (Oct. 17, 1997).
Fero, M. et al., "A syndrome of multiorgan hyperplasia with features of gigantism, tumorigenesis, and female sterility in $p27^{Kip1}$-deficient mice," *Cell*, 85(5):733-744 (May 31, 1996).
Friedrich, G. and Soriano, P., "Promoter traps in embryonic stem cells: genetic screen to identify and mutate development genes in mice," *Genes Dev.*, 5(9):1513-1523 (Sep. 1991).
Gould, K. et al., "Phosphorylation at Thr167 is required for *Schizosaccharomyces pombe* $p34^{cdc2}$ function," *EMBO J.*, 10(11):3297-3309 (Nov. 1991).
Hannon, G. and Beach, D., "$p15^{INK4B}$ is a potential effector of TGF-β-induced cell cycle arrest," *Nature*, 371(6494):257-261 (Sep. 15, 1994).
Hatakeyama, M. et al., "The cancer cell and the cycle clock," *Cold Spring Harb. Symp. Quant. Biol.*, 59:1-10 (1994).
Hengst, L., and Reed, S., "Translational control of $p27^{Kip1}$ accumulation during the cell cycle," *Science*, 271(5257):1861-1864 (Mar. 29, 1996).
Holmes, J. and Solomon, M., "A predictive scale for evaluating cyclin-dependent kinase substrates. A comparison of $p34^{cdc2}$ and $p33^{cdk2}$," *J. Biol. Chem.*, 271(41):25240-25246 (Oct. 11, 1996).
Jeffrey, P., et al., "Mechanism of CDK activation revealed by the structure of a cyclinA-CDK2 complex," *Nature*, 376(6538):313-320 (Jul. 27, 1995).

(Continued)

*Primary Examiner*—Valarie Bertoglio
(74) *Attorney, Agent, or Firm*—Townsend and Townsend and Crew LLP

(57) ABSTRACT

The present invention relates to germ line and somatic cells comprising a mutant $p27_{kip1}$ protein lacking a Cdk2 phosphorylation site. Also provided are transgenic animals and methods of making such transgenic animals which have increased size and/or growth rate.

6 Claims, No Drawings

OTHER PUBLICATIONS

Kato, J. et al., "Cyclic AMP-induced G1 phase arrest mediated by an inhibitor (p27$^{Kip1}$) of cyclin-dependent kinase 4 activation," *Cell*, 79(3):487-496 (Nov. 4, 1994).

Koff, A. et al., "Negative regulation of G1 in mammalian cells: inhibition of cyclin E-dependent kinase by TGF-β," *Science*, 260(5107):536-539 (Apr. 23, 1993).

Lee, MH et al., "Cloning of p57$^{KIP2}$, a cyclin-dependent kinase inhibitor with unique domain structure and tissue distribution," *Genes Dev.*, 9(6):639-649 (Mar. 15, 1995).

Leone, G. et al., "Myc and Ras collaborate in incducing accumulation of active cyclin E/Cdk2 and E2F," *Nature*, 387(6631):422-426 (May 22, 1997).

Malek, N. et al., "A mouse knock-in model exposes sequential proteolytic pathways that regulate p27$^{Kip1}$ in G1 and S phase," *Nature*, 413(6853):323-327 (Sep. 20, 2001).

Millard, S.S. et al., "A U-rich element in the 5' untranslated region is necessary for the translation of p27 mRNA," *Mol. Cell. Biol.*, 20(16):5947-5959 (Aug. 2000).

Millard, S.S. et al., "Enhanced ribosomal association of p27$^{Kip1}$ mRNA is a mechanism contributing to accumulation during growth arrest," *J. Biol. Chem.*, 272(11):7093-7098 (Mar. 14, 1997).

Montagnoli, A. et al., "Ubiquitination of p27 is regulated by Cdk-dependent phosphorylation and trimeric complex formation," *Genes Dev.*, 13(9):1181-1189 (May 1, 1999).

Morgan, D., "Principles of CDK regulation," *Nature*, 374(6518):131-134 (Mar. 9, 1995).

Morimoto, M. et al., "Modification of cullin-1 by ubiquitin-like protein Nedd8 enhances the activity of SCF$^{skp2}$ toward p27$^{Kip1}$," *Biochem. Biophys. Res. Commun.*, 270(3):1093-1096 (Apr. 21, 2000).

Müller, D. et al., "Cdk2-dependent phosphorylation of p27 facilitates its Myc-induced release from cyclin E/cdk2 complexes," *Oncogene*, 15(21):2561-2576 (Nov. 20, 1997).

Nagy, A. et al., "Dissecting the role of *N-myc* in development using a single targeting vector to generate a series of alleles," *Curr. Biol.*, 8(11):661-664 (May 21, 1998).

Nourse, J. et al., "Interleukin-2-mediated elimination of the p27$^{Kip1}$ cyclin-dependent kinase inhibitor prevented by rapamycin," *Nature*, 372(6506):570-573 (Dec. 8, 1994).

O'Hagan, R. et al., "Myc-enhanced expression of Cul1 promotes ubiquitin-dependent proteolysis and cell cycle progression," *Genes Dev.*, 14(17):2185-2191 (Sep. 1, 2000).

Pardee, A., "A restriction point for control of normal animal cell proliferation," *Proc. Natl. Acad. Sci. USA.*, 71(4):1286-1290 (Apr. 1974).

Polyak, K. et al., "Cloning of p27$^{Kip1}$, a cyclin-dependent kinase inhibitor and a potential mediator of extracellular antimitogenic signals," *Cell*, 78(1):59-66 (Jul. 15, 1994).

Rolfe, M. et al., "The ubiquitin-mediated proteolytic pathway as a therapeutic area," *J. Mol. Med.*, 75(1):5-17 (Jan. 1997).

Serrano, M. et al., "A new regulatory motif in cell-cycle control causing specific inhibition of cyclin D/CDK4," *Nature*, 366(6456):704-707 (Dec. 16, 1993).

Sheaff, R. et al., "Cyclin E-CDK2 is a regulator of p27$^{Kip1}$," *Genes Dev.*, 11(11):1464-1478 (Jun. 1, 1997).

Sherr, C. and Roberts, J. "CD inhibitors: positive and negative regulators of $G_1$-phase progression," *Genes Dev.*, 13(12):1501-1512 (Jun. 15, 1999).

Shilo, B.Z. and Weinberg, R., "DNA sequences homologous to vertebrate oncogenes are conserved in *Drosophilia melanogaster*," *Proc. Natl. Acad. Sci. USA.*, 78(11):6789-6792 (Nov. 1981).

Skowyra, D. et al., "F-box proteins are receptors that recruit phosphorylated substrates to the SCF ubiquitin-ligase complex," *Cell*, 91(2):209-219 (Oct. 17, 1997).

Solomon, M. et al., "CAK, the p34$^{cdc2}$ activating kinase, contains a protein identical or closely related to p40$^{MO15}$," *EMBO J.*, 12(8):3133-3142 (Aug. 1993).

Solomon, M. et al., "Role of phosphorylation in p34$^{cdc2}$ activation: Identification of an activating kinase," *Mol. Biol. Cell*, 3(1):13-27 (Jan. 1992).

Sutterlüty, H. et al., "p45$^{SKP2}$ promotes p27$^{Kip1}$ degradation and induces S phase in quiescent cells," *Nat. Cell Biol.*, 1(4):207-214 (Aug. 1999).

Torchinsky, C. et al., "Regulation of p27Kip1 during gentamicin mediated hair cell death," *J. Neurocytol.*, 28:913-924 (Oct.-Nov. 1999).

Toyoshima, H. and Hunter, T., "p27, a novel inhibitor of G1 cyclin-Cdk protein kinase activity, is related to p21," *Cell*, 78(1):67-74 (Jul. 15, 1994).

Tsvetkov, L. et al., "p27$^{Kip1}$ ubiquitination and degradation is regulated by the SCF$^{Skp2}$ complex through phosphorylated Thr187 in p27," *Curr. Biol.*, 9(12):661-664 (Jun. 7, 1999).

Vlach, J. et al., "Growth arrest by the cyclin-dependent kinase inhibitor p27$^{Kip1}$ is abrogated by c-Myc," *EMBO J.*, 15(23)6595-6604 (Dec. 2, 1996).

Xiong, Y. et al., "p21 is a universal inhibitor of cyclin kinases," *Nature*, 366(6456):701-704 (Dec. 16, 1993).

\* cited by examiner

SEQUENCE LISTING

<160> NUMBER OF SEQ ID NOS: 12

<210> SEQ ID NO 1
<211> LENGTH: 30
<212> TYPE: DNA
<213> ORGANISM: Artificial Sequence
<220> FEATURE:
<223> OTHER INFORMATION: PCR Primer

<400> SEQUENCE: 1
gagcaggttt gttggcagtc gtacacctcc         30

<210> SEQ ID NO 2
<211> LENGTH: 24
<212> TYPE: DNA
<213> ORGANISM: Artificial Sequence
<220> FEATURE:
<223> OTHER INFORMATION: PCR Primer

<400> SEQUENCE: 2
cgtgggatca ttgttttct cttg         24

<210> SEQ ID NO 3
<211> LENGTH: 27
<212> TYPE: DNA
<213> ORGANISM: Artificial Sequence
<220> FEATURE:
<223> OTHER INFORMATION: PCR Primer

<400> SEQUENCE: 3
ccaatatggc ggtggaaggg aggctga         27

<210> SEQ ID NO 4
<211> LENGTH: 48
<212> TYPE: PRT
<213> ORGANISM: Artificial Sequence
<220> FEATURE:
<223> OTHER INFORMATION: Consensus Sequence

<400> SEQUENCE: 4

Ile Arg Lys Arg Pro Ala Thr Asp Asp Ser Ser Thr Gln Asn Lys Arg
1               5                   10                  15

Ala Asn Arg Thr Glu Glu Asn Val Ser Asp Gly Ser Pro Asn Ala Gly
            20                  25                  30

Ser Val Glu Gln Thr Pro Lys Lys Pro Gly Leu Arg Arg Gln Thr
            35                  40                  45

<210> SEQ ID NO 5
<211> LENGTH: 48
<212> TYPE: PRT
<213> ORGANISM: Homo sapiens;

<400> SEQUENCE: 5

Ile Arg Lys Arg Pro Ala Thr Asp Asp Ser Ser Thr Gln Asn Lys Arg
1               5                   10                  15

Ala Asn Arg Thr Glu Glu Asn Val Leu Asp Gly Ser Pro Asn Ala Gly
            20                  25                  30

Ser Val Glu Gln Thr Pro Lys Lys Pro Gly Leu Arg Arg Gln Thr
            35                  40                  45

<210> SEQ ID NO 6
<211> LENGTH: 48
<212> TYPE: PRT
<213> ORGANISM: Homo sapiens;

<400> SEQUENCE: 6

Ile Arg Lys Arg Pro Ala Thr Asp Asp Ser Ser Thr Gln Asn Lys Arg
1               5                   10                  15

Ala Asn Arg Thr Glu Glu Asn Val Ser Asp Gly Ser Pro Asn Ala Gly
            20                  25                  30

Ser Val Glu Gln Thr Pro Lys Lys Pro Gly Leu Arg Arg Gln Thr
            35                  40                  45

<210> SEQ ID NO 7
<211> LENGTH: 48
<212> TYPE: PRT
<213> ORGANISM: Feline;

<400> SEQUENCE: 7

Ile Arg Lys Arg Pro Ala Thr Asp Asp Ser Ser Pro Gln Asn Lys Arg
1               5                   10                  15

Ala Asn Arg Thr Glu Glu Asn Val Ser Asp Gly Ser Pro Asn Ala Gly
            20                  25                  30

Ser Val Glu Gln Thr Pro Lys Lys Pro Gly Leu Arg Arg Gln Thr
            35                  40                  45

<210> SEQ ID NO 8
<211> LENGTH: 48
<212> TYPE: PRT
<213> ORGANISM: Porcine;

<400> SEQUENCE: 8

Ile Arg Lys Arg Pro Ala Thr Asp Asp Ser Ser Pro Gln Asn Lys Arg
1               5                   10                  15

Ala Asn Arg Thr Glu Glu Asn Val Ser Asp Gly Ser Pro Asn Ser Ala
            20                  25                  30

-continued

```
Ser Val Glu Gln Thr Pro Lys Lys Pro Gly Leu Arg Arg Arg Gln Thr
        35                  40                  45

<210> SEQ ID NO 9
<211> LENGTH: 46
<212> TYPE: PRT
<213> ORGANISM: Murine;

<400> SEQUENCE: 9

Met Arg Lys Arg Pro Ala Ala Glu Asp Ser Ser Ser Gln Asn Lys Arg
1               5                   10                  15

Ala Asn Arg Thr Glu Glu Asn Val Ser Asp Gly Ser Pro Asn Ala Gly
            20                  25                  30

Thr Val Glu Gln Thr Pro Lys Lys Pro Gly Leu Arg Arg Gln
        35                  40                  45

<210> SEQ ID NO 10
<211> LENGTH: 48
<212> TYPE: PRT
<213> ORGANISM: Hamster;

<400> SEQUENCE: 10

Met Arg Lys Arg Pro Ala Ala Asp Asp Ser Ser Ser Gln Asn Lys Arg
1               5                   10                  15

Ala Asn Arg Thr Glu Glu Asn Val Ser Asp Gly Ser Leu Asn Ala Gly
            20                  25                  30

Ser Val Glu Gln Thr Pro Lys Lys Pro Gly Leu Arg Arg His Gln Thr
        35                  40                  45

<210> SEQ ID NO 11
<211> LENGTH: 46
<212> TYPE: PRT
<213> ORGANISM: Ratus;

<400> SEQUENCE: 11

Met Arg Lys Arg Pro Ala Ala Glu Asp Ser Ser Ser Gln Asn Lys Arg
1               5                   10                  15

Ala Asn Arg Thr Glu Glu Asn Val Ser Asp Gly Ser Pro Asn Ala Gly
            20                  25                  30

Thr Val Glu Gln Thr Pro Lys Lys Pro Gly Leu Arg Arg Gln
        35                  40                  45

<210> SEQ ID NO 12
<211> LENGTH: 46
<212> TYPE: PRT
<213> ORGANISM: Ratus;

<400> SEQUENCE: 12

Met Arg Lys Arg Pro Ala Ala Glu Asp Ser Ser Ser Gln Asn Lys Arg
1               5                   10                  15

Ala Ser Arg Thr Glu Glu Asn Val Ser Asp Gly Ser Pro Asn Ala Gly
            20                  25                  30

Thr Val Glu Gln Thr Pro Lys Lys Pro Gly Leu Arg Arg Gln
        35                  40                  45
```

COMPOSITIONS AND METHODS FOR INCREASING ANIMAL SIZE GROWTH RATE

RELATED APPLICATIONS

This is a U.S. National Stage Application under 35 U.S.C. §371 of International Application No. PCT/US03/02423, filed on Jan. 27, 2003, which claims the benefit of U.S. Provisional Patent Application Ser. No. 60/352,391, filed on Jan. 28, 2002, the disclosures of which are incorporated herein by reference.

STATEMENT AS TO RIGHTS TO INVENTIONS MADE UNDER FEDERALLY SPONSORED RESEARCH AND DEVELOPMENT

This work was supported by a grant from the National Institutes of Health (Grant No. CA-67893. The government may have certain rights in the invention.

BACKGROUND OF THE INVENTION

Animal cells have both a proliferating phase and a quiescent phase. Cells can shift from the proliferating phase to the quiescent phase during a brief window in the cell cycle. Depending on their position in the cell cycle, cells deprived of mitogens such as those present in serum can undergo immediate cell cycle arrest, or they can complete the current mitotic cycle and arrest in the next cell cycle. The transition from mitogen-dependence to mitogen-independence occurs in mid- to late-G1 phase of the cell cycle. Anti-mitogenic signals can cause the cell cycle to arrest at a kinetically common point. In particular, in early G1, cells can exit the cell cycle. Cell cycle commitment (autonomy from mitogenic signals) occurs in mid-G1.

The transition of cells through G1 and entry into S phase requires the action of cyclin-dependent kinases (Cdks). Growth inhibitory signals have been shown to prevent activation of these Cdks during G1 (Serrano et al., *Nature* 366: 704-07 (1993); Hannon and Beach, *Nature* 371:257-61 (1994); Xiong et al., *Nature* 366:701-04 (1993); Polyak et al., *Cell* 78:59-66 (1994); Lee et al., *Genes & Development* 9:639-49 (1995); Koff et al., *Science* 260:536-39 (1993)). The catalytic activity of Cdks is known to be regulated by two general mechanisms: protein phosphorylation and association with regulatory subunits (Gould et al., *EMBO J.* 10:3297-309 (1991); Solomon et al., *EMBO J.* 12:3133-42 (1993); Solomon et al., *Mol. Biol. Cell* 3:13-27 (1992); Jeffrey et al., *Nature* 376:313-20 (1995); Morgan, *Nature* 374:131-34 (1995)). Among the regulatory subunits, the association of Cdks with inhibitory CKI subunits (Cyclin-dependent Kinase Inhibitors) has been most closely correlated with the effect of mitogen depletion on cell proliferation and Cdk activity.

The CKI directly implicated in mitogen-dependent Cdk regulation is $p27^{Kip1}$ (Polyak et al., *Cell* 78:59-66 (1994); Toyoshima and Hunter, *Cell* 78:67-77 (1994)). Wildtype $p27^{Kip1}$ protein accumulates to high levels in quiescent cells, and is rapidly destroyed after quiescent cells are re-stimulated with specific mitogens (Nourse et al., *Nature* 372:570-73 (1994); Kato et al., *Cell* 79:487-96 (1994)). The destruction of $p27^{Kip1}$ is controlled by phosphorylation of $p27^{Kip1}$ at threonine 187 (T187). T187 is phosphorylated by Cdk2 to create a binding site for a Skp2-containing ubiquitin-protein ligase known as the Skp1-cullin-F-box protein ligase (SCF) (Feldman et al., *Cell* 91:221-30 (1997); Bai et al., *Cell* 86:263-74 (1996); Skowyra et al., *Cell* 91:209-19 (1997)). Ubiquitination of $p27^{Kip1}$ by the SCF then results in $p27^{Kip1}$ degradation by the proteosome (Sutterluty et al., *Nature Cell Biol.* 1:207-14 (1999); Rolfe et al., *J. Mol. Med.* 75:5-17 (1997); Carrano et al., *Nature Cell Biol.* 1:193-99 (1999); Tsvetkov et al., *Curr. Biol.* 9:661-64 (1999)).

The destruction of $p27^{Kip1}$ was thought to be required for entry into S phase. Moreover, constitutive expression of $p27^{Kip1}$ in cultured cells causes the cell cycle to arrest in G1 (Polyak, supra; Toyoshima and Hunter, supra). Thus, based on these observations, it was expected that cells harboring a null allele of $p27^{Kip1}$ would arrest G1. It was surprising, therefore, that animals harboring a null allele of the $p27^{Kip1}$ gene survived. Indeed, such animals were larger than normal (increased animal size) and without apparent gross morphologic abnormalities. (Fero et al., *Cell* 85:733-44 (1996); U.S. Pat. No. 5,958,769; the disclosures of which are incorporated by reference herein.) The advantages of producing larger animals are readily apparent, and include increase meat, milk and/or egg production.

Decreased levels of $p27^{Kip1}$ in animals, however, cause certain minor defects, such as an ovulatory defect, and resulting female sterility, increased pituitary tumorigenesis and disrupted retinal architecture. (Fero et al., supra.) These defects can interfere with some uses of such animals. Thus, there is a need for alternative mutant alleles of $p27^{Kip1}$, and of methods of using such mutant alleles, that promote increased animal size or growth rate without these side effects.

SUMMARY OF THE INVENTION

The present invention relates to nucleic acids encoding a mutant $p27^{Kip1}$ protein that lacks a Cdk2 phosphorylation site, and to cells harboring mutant $p27^{Kip1}$ genes. In related aspects, transgenic cells and transgenic animals are provided that have one or more mutant $p27^{Kip1}$ genes encoding protein that lacks a Cdk2 phosphorylation site.

In one aspect, isolated transgenic cells are provided comprising a mutant $p27^{Kip1}$ gene lacking a Cdk2 phosphorylation site. The mutant $p27^{Kip1}$ gene encodes a mutant $p27^{Kip1}$ protein having a longer half-life in S phase than wildtype $p27^{Kip1}$ polypeptide. In certain embodiments, the mutant $p27^{Kip1}$ polypeptide can inhibit Cdk2 in vitro kinase activity. In an embodiment, the mutant $p27^{Kip1}$ polypeptide is $p27^{T187A}$.

The mutant $p27^{Kip1}$ gene can be located, for example, at an endogenous $p27^{Kip1}$ locus; the endogenous locus can be heterozygous or homozygous for the mutant $p27^{Kip1}$ gene. The transgenic cell can be, for example, a primordial germ cell, oocyte, egg, spermatocyte, sperm cell, fertilized egg, zygote, embryonic stem cell, or somatic cell. The transgenic cell can also be progeny of any of these.

In another aspect, non-human, transgenic animals are provided which comprise a nucleic acid sequence encoding a mutant $p27^{Kip1}$ protein lacking a Cdk2 phosphorylation site. In an embodiment, the mutant $p27^{Kip1}$ protein is $p27^{T187A}$. The transgenic animal can be, for example, a primate, mammal, bovine, porcine, ovine, equine, avian, rodent, fowl, piscine, or crustacean. In certain embodiments, the transgenic animal is a farm animal, such as a chicken, cow, bull, horse, pig, sheep, goose or duck.

In a related aspect, a transgenic, non-human animal is provided whose genome comprises a $p27^{Kip1}$ gene and expresses a mutant $p27^{Kip1}$ polypeptide having a longer half-life in S phase than wildtype p27 polypeptide. Expression of the mutant $p27^{Kip1}$ polypeptide results in increased size or growth rate of the animal. The transgenic animal, can be, for example, a primate, mammal, bovine, porcine, ovine, equine, avian, rodent, fowl, piscine, or crustacean. In certain embodiments, the transgenic animal is a farm animal, such as a chicken, cow, bull, horse, pig, sheep, goose or duck.

Methods of increasing the size or growth rate of a non-human, transgenic animal are also provided. Such methods generally include stably introducing into a genome of an animal cell a mutant p27$^{Kip1}$ gene lacking a Cdk2 phosphorylation site; and producing an animal from the animal cell. In an embodiment, the method further includes transferring a nucleus from the animal cell into a second cell from which an animal can be reconstituted; and allowing the second cell to develop into an immature animal. The immature animal typically is larger than an immature animal not having the mutant p27$^{Kip1}$ gene. The second cell, can be, for example, an enucleated fertilized egg.

In another embodiment, the mutant p27$^{Kip1}$ gene can be homologously integrated at an endogenous p27$^{Kip1}$ locus in the animal cell. The mutant p27$^{Kip1}$ gene can be homologous or heterologous to the animal cell, and can be integrated at an endogenous p27$^{Kip1}$ locus or at a non-p27$^{Kip1}$ locus. The mutant p27$^{Kip1}$ gene can encode, for example, p27$^{T187A}$ protein.

The animal cell can be, for example, a germ cell, a totipotent cell, a stem cell, an embryonic stem cell, a pluripotent stem cell, a fetal cell, a primordial germ cell, an oocyte, an egg, a spermatocyte, a sperm cell, a fertilized egg, a zygote, a blastomere, or a somatic cell. The animal cell can be a vertebrate cell, such as, for example, from a primate, mammal, bovine, porcine, ovine, equine, avian, rodent, fowl, piscine, or crustacean. Exemplary animals include a chicken, hen, rooster, cow, bull, duck or goose.

Mutant genes can be introduced into cells by electroporation, microinjection, lipofection, transfection, biolistics, and the like. The mutant p27$^{Kip1}$ genes can be introduced alone or as part of an expression cassette that includes, for example, a heterologous promoter operably associated with an open reading frame encoding a mutant p27$^{Kip1}$ gene operably associated with a polyadenylation sequence. The expression cassette can also optionally include a selectable marker, such as the neomycin resistance gene. In an embodiment, the expression cassette can be introduced into a cell using a viral vector.

In another aspect, a method for making a large fowl is provided. The method includes introducing a mutant p27$^{Kip1}$ gene lacking a Cdk2 phosphorylation site into the genome of a fowl cell by contacting in vivo a blastodermal cell of a fertilized cell with the mutant p27$^{Kip1}$ gene, wherein the p27$^{Kip1}$ gene is introduced directly into the germinal disk of the egg. Suitable fowl cells include those from chickens, ostriches, emus, turkeys, ducks, geese, quail, parrots, parakeets, cockatoos or cockatiels.

A further understanding of the present invention will be obtained by reference to the following description that sets forth illustrative embodiments.

DESCRIPTION OF THE SPECIFIC EMBODIMENTS

The present invention relates to nucleic acids encoding a mutant p27$^{Kip1}$ protein that lacks a Cdk2 phosphorylation site and to cells harboring mutant p27$^{Kip1}$ genes. In related aspects, transgenic cells and transgenic animals are provided that have one or more mutant p27$^{Kip1}$ genes encoding protein that lacks a Cdk2 phosphorylation site.

The p27$^{Kip1}$ protein is phosphorylated by a Cdk at a phosphorylation site to create a recognition sequence for a SCF (e.g., Cdk2). The absence or alteration of the Cdk2 phosphorylation site in p27$^{Kip1}$ reduces or eliminates phosphorylation. Although the mutant p27$^{Kip1}$ polypeptide is degraded in mid-G1 by the same pathway that degrades wildtype p27, the mutant p27$^{Kip1}$ polypeptide has a longer half life in the S phase of the cell cycle as compared with wildtype p27$^{Kip1}$ polypeptide. Yet, the mutant p27$^{Kip1}$ protein can retain other functions, such as the ability to inhibit Cdk2 in vitro kinase activity.

In one aspect of the invention, isolated mutant p27$^{Kip1}$ genes are provided for introduction into animal cells. (The term "isolated" refers to a molecule, such as a nucleic acid, or cell, that has been removed from its natural cellular environment. For example, an isolated nucleic acid is typically at least partially purified from other cellular nucleic acids, polypeptides and other constituents.) The mutant p27$^{Kip1}$ gene encodes a p27$^{Kip1}$ polypeptide lacking a Cdk2 phosphorylation site, such that less than about 10% of the mutant p27$^{Kip1}$ polypeptide is phosphorylated at the Cdk2 phosphorylation site. In certain embodiments, phosphorylation at the Cdk2 phosphorylation site is less than about 5%, or less than about 1%.

The Cdk2 phosphorylation site can be defined by the following four amino acid consensus sequence: (Ser/Thr) ProXaa(Lys/Arg) or the consensus sequence (Ser/Thr) ProXaa(Lys/Arg/His/Pro), wherein Xaa can be any amino acid residue. (See, e.g., Holmes and Solomon, *J. Biol. Chem.* 271:25240-46 (1996).) Phosphorylation can be inhibited by substitutions, insertions and/or deletions (e.g., 1-3 amino acid insertions or deletions).

Referring to Table 1, the Cdk2 phosphorylation site, including the phosphorylated residue, is generally conserved in p27$^{Kip1}$ polypeptides. As shown in the table, an asterisk indicates the position of a conserved threonine at position 187 of the human Cdk2 phosphorylation site. As used herein, this conserved threonine is referred to as threonine 187 (T187), although the skilled artisan will appreciate that this conserved residue may not be at position 187 in all p27$^{Kip1}$ polypeptides. For example, in the mouse, hamster and rat polypeptide sequences, the conserved, phosphorylated residue is at position 186, although it is identifiable by sequence alignment and by biochemical analysis, as discussed in the Examples (infra). Thus, the terms "T187," "T187A" and position "187" are merely

TABLE 1

| Consensus | | 151 | IRKRPATDDSSTQNKRANRTEENVSDGSPNAGSVEQTPKKPGLRRRQT | 198 (SEQ ID NO:4) |
|---|---|---|---|---|
| Genbank | Species | | Residues | |
| 7769665 | Human | 151 | .........................L...................... | 198 SEQ ID NO:5) |
| 4757962 | Human | 151 | .................................................. | 198 SEQ ID NO:6) |
| 12805035 | Human | 151 | .................................................. | 198 SEQ ID NO:6) |

TABLE 1-continued

| | | | | | | |
|---|---|---|---|---|---|---|
| 2135228 | Human | 151 | ............................................. | 198 | SEQ ID NO:6) |
| 3913222 | Cat | 151 | ...........P................................. | 198 | SEQ ID NO:7) |
| 13429931 | Pig | 151 | ...........P...................SA............ | 198 | SEQ ID NO:8) |
| 6753386 | Mouse | 151 | M.....AE...S....................T...........Q | 196 | SEQ ID NO:9) |
| 2493565 | Hamster | 151 | M.....A....S..................L.............H.. | 198 | SEQ ID NO:10) |
| 2102649 | Rat | 151 | M.....AE...S....................T...........Q | 196 | SEQ ID NO:11) |
| 2281010 | Rat | 151 | M.....AE...S.....S..............T...........Q | 196 | SEQ ID NO:12) | shorthand for this conserved threonine residue position and not to be limited to amino acid 187 of a $p27^{Kip1}$ polypeptide, or the corresponding codon in a $p27^{Kip1}$ gene.

A Cdk2 phosphorylation site in a $p27^{Kip1}$ polypeptide can be identified, for example, by biochemical analysis. (See, e.g., Holmes and Solomon, supra.) A Cdk2 phosphorylation site in a $p27^{Kip1}$ gene and/or polypeptide sequence also can be identified by alignment with known $p27^{Kip1}$ gene and/or polypeptide sequences. For example, an alignment can be performed by the local homology algorithm of Smith and Waterman (*Adv. Appl. Math.* 2:482 (1981), which is incorporated by reference herein in its entirety), by the homology alignment algorithm of Needleman and Wunsch (*J. Mol. Biol.* 48:443-53 (1970), which is incorporated by reference herein in its entirety), by the search for similarity method of Pearson and Lipman (*Proc. Natl. Acad. Sci. USA* 85:2444-48 (1988), which is incorporated by reference herein in its entirety), by computerized implementations of these algorithms (e.g., GAP, BESTFIT, FASTA, and TFASTA in the Wisconsin Genetics Software Package (Accelrys), or by visual inspection.

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (*J. Mol. Evol.* 25:351-60 (1987), which is incorporated by reference herein in its entirety). The method used is similar to the method described by Higgins and Sharp (*Comput. Appl. Biosci.* 5:151-53 (1989), which is incorporated by reference herein in its entirety). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for aligning sequences, and for determining percent sequence identity and sequence similarity, is the BLAST algorithm, which is described by Altschul et al. (*J. Mol. Biol.* 215:403-410 (1990), which is incorporated by reference herein in its entirety). (See also Zhang et al., *Nucleic Acid Res.* 26:3986-90 (1998; Altschul, et al., *Nucleic Acid Res.* 25:3389-402 (1997), which are incorporated by reference herein in their entirety). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as default parameters a wordlength (W) of 11, the BLOSUM62 scoring matrix (see Henikoff and Henikoff, *Proc. Natl. Acad. Sci. USA* 89:10915-19 (1992), which is incorporated by reference herein in its entirety) alignments (B) of 50, expectation (E) of 10, M=5, N=−4, and a comparison of both strands. The skilled artisan will appreciate, however, that other parameters can be used.

The isolated, mutant $p27^{Kip1}$ genes can be, for example, genomic DNA, cDNA, RNA, mRNA, and the like, as well as fragments of any of these. The mutant $p27^{Kip1}$ genes can be polynucleotides or nucleic acids or other polymers composed of a multiplicity of nucleotide units (ribonucleotide or deoxyribonucleotide or related structural variants) linked via phosphodiester bonds. Mutant genes can be of substantially any length, typically from about twelve (12) nucleotides to about $10^9$ nucleotides or larger, that do not encode a Cdk2 phosphorylation site. In one embodiment, a fragment of a mutant $p27^{Kip1}$ gene has at least 50 contiguous nucleotides; in other embodiments, the fragment of the mutant $p27^{Kip1}$ gene is at least 100 nucleotides, at least 200 nucleotides, at least 500 nucleotides, at least 1000 nucleotides, or more of the gene. In related embodiments, the mutant $p27^{Kip1}$ gene is at least an exon, a cDNA, or a fall length genomic p27$^{Kip1}$ gene, lacking a Cdk2 phosphorylation site.

Mutant p27$^{Kip1}$ genes also include derivatives, such as those based on all possible codon choices for an amino acid(s) that, when expressed from a mutant p27$^{Kip1}$ gene, results in the expression of a mutant protein in which Cdk-mediated phosphorylation is inhibited. At amino acid positions outside the Cdk2 phosphorylation site, mutant p27$^{Kip1}$ gene derivatives can include those based on all possible codon choices for the same amino acid and codon choices based on conservative amino acid substitutions. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, *Proteins*, W. H. Freeman and Company (1984).) In addition, individual substitutions, deletions or additions that alter, add or delete a single amino acid or a small percentage of amino acids in an encoded sequence are also "conservative substitutions."

In certain embodiments, mutant p27$^{Kip1}$ genes be synthesized, or chemically or biochemically modified (e.g., can contain non-natural or derivatized nucleotide bases). Such modifications include, for example, labels, methylation, substitutions of one or more of the naturally-occurring nucleotides with an analog, internucleotide modifications such as uncharged linkages (e.g., methyl phosphonates, phosphotriesters, phosphoamidates, carbamates, and the like), charged linkages (e.g. phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like).

The mutant p27$^{Kip1}$ gene(s) can be homologous or heterologous to the cell or the animal. As used herein, the term "homologous" p27$^{Kip1}$ gene refers to a p27$^{Kip1}$ gene derived from the same species as the cell or animal. A "heterologous" p27$^{Kip1}$ gene refers to a p27$^{Kip1}$ gene from a different species. For example, if the animal is a chicken, a homologous mutant p27$^{Kip1}$ gene is derived from a chicken p27$^{kip1}$ gene, while a heterologous mutant p27$^{Kip1}$ gene is derived, for example, from a mouse p27$^{Kip1}$ gene.

The mutant p27$^{Kip1}$ gene can be prepared by, for example, mutagenizing a wild-type p27$^{Kip1}$ gene at one or more positions in the Cdk2 phosphorylation site. In various embodiments, the p27$^{Kip1}$ gene is human, primate, mammalian, avian, porcine, ovine, bovine, fowl, rodent, fish, crustacean, and the like. In specific embodiments, the p27$^{Kip1}$ is from a sheep, goat, horse, cow, bull, pig, rabbit, guinea pig, hamster, rat, gerbil, mouse, chicken, ostrich, emu, turkey, duck, goose, quail, parrot, parakeet, cockatoo, cockatiel, trout, cod, salmon, crab, king crab, lobster, shrimp, and the like. p27$^{Kip1}$ gene sequences are disclosed for example, in the GenBank database under accession numbers gi|7769665|, gi|4757962|, gi|12805035|, gi|2135228|, gi|3913222|, gi|13429931|, gi|6753386|, gi|2493565|, gi|2102649|, and gi|2281010|, which are incorporated by reference herein in their entirety. p27$^{Kip1}$ polypeptide sequences are disclosed, for example, in the GenBank database under accession numbers AAF69497.1, NP_004055.1, AAH01971.1, I52718, O19001, BAB39725.1, NP_034005.1, Q60439, BAA19960.1, and BAA21561.1 (the disclosures of which are incorporated by reference herein in their entirety).

p27$^{Kip1}$ genes can be readily isolated by methods known to the skilled artisan. (See generally Sambrook et al., *Molecular Cloning, A Laboratory Manual*, 3rd ed., Cold Spring Harbor Publish., Cold Spring Harbor, N.Y. (2001); Ausubel et al., *Current Protocols in Molecular Biology*, 4th ed., John Wiley and Sons, New York (1999); which are incorporated by reference herein in their entirety.) Specific embodiments for the isolation of p27$^{Kip1}$ genes, presented as example but not by way of limitation, are described below.

p27$^{Kip1}$ genes can be isolated, for example, by polymerase chain reaction (PCR) to amplify the p27$^{Kip1}$ gene, or a portion thereof, from a genomic or cDNA library. Oligonucleotide primers representing known p27$^{Kip1}$ sequences can be used as primers in PCR. In a typical embodiment, the oligonucleotide primers represent at least a fragment of conserved segments of identity between p27$^{Kip1}$ genes of different species. Synthetic oligonucleotides can be utilized as primers to amplify particular oligonucleotides within a p27$^{Kip1}$ gene by PCR sequences from any suitable source (e.g., RNA or DNA), typically a cDNA library or mRNA of potential interest. PCR can be carried out, for example, by use of a Perkin-Elmer Cetus thermal cycler and Taq polymerase (Gene Amp). Degenerate primers can be designed for use in the PCR reactions. For example, the CODEHOP strategy of Rose et al. (*Nucl. Acids Res.* 26:1628-35 (1998), which is incorporated by reference herein in its entirety) can be used to design degenerate PCR primers using multiply-aligned sequences as a reference. Methods for performing PCR and related methods are well known in the art. (See, e.g., U.S. Pat. Nos. 4,683,202; 4,683,195 and 4,800,159; Innis et al., *PCR Protocols: A Guide to Methods and Applications*, Academic Press, Inc., San Diego, Calif. (1989); Innis et al., *PCR Applications: Protocols for Functional Genomics*, Academic Press, Inc., San Diego, Calif. (1999); White (ed.), *PCR Cloning Protocols: From Molecular Cloning to Genetic Engineering*, Humana Press, (1996); EP 320 308; the disclosures of which are incorporated by reference herein in their entirety.)

In an embodiment, degenerate primers are used to isolate the p27$^{Kip1}$ cDNA from an avian species. Avian species are known to have p27$^{Kip1}$. (See Torchinsky et al., *J. Neurocytol.* 28:913-24 (1999).) Briefly, an alignment of multiple p27$^{Kip1}$ polypeptide sequences from different animals is prepared and used to visually identify blocks of sequences having low codon degeneracy (see Rose et al. (supra)). The CODEHOP strategy of Rose et al. (supra) is used to design degenerate primers based on the blocks of low codon degeneracy. Pools of primers varying in redundancy from 2 fold to about 32 fold are prepared. A hemi-nested PCR strategy is used to amplify fragments from an avian chicken cDNA library (e.g., a chicken or hyacinth macaw library from Stratagene). Briefly, PCR is performed at 55° C. using the primer pools. (See, e.g., Rose et al. (supra); Rose et al., *J. Virology* 71:4138-44 (1997).) PCR amplification products can be detected, for example, by agarose gel electrophoresis. The identity of the PCR amplification products can be confirmed by DNA sequence analysis. Once the identify of the PCR amplification products is confirmed, the amplification products can be used to isolate full length p27$^{Kip1}$ cDNA from the avian cDNA library. (See, e.g., Sambrook et al., supra; Ausubel et al., supra.)

For expression cloning (a technique commonly known in the art), an expression library is constructed by methods known in the art. For example, mRNA is isolated, cDNA is prepared and then ligated into an expression vector (e.g., a bacteriophage derivative) such that it is capable of being expressed by the host cell into which it is then introduced. Various screening assays can then be used to select for the expressed p27$^{Kip1}$ polypeptide. In one embodiment, polyclonal antibodies against a mammalian p27$^{Kip1}$ polypeptide (see, e.g. U.S. Pat. No. 6,242,575; the disclosure of which is incorporated by reference herein in its entirety) are used to screen a chicken cDNA expression library (e.g., from Strategene) to identify avian p27$^{Kip1}$ genes.

Alternatively, p27$^{Kip1}$ genes can be isolated by hybridization using a heterologous p27$^{Kip1}$ nucleic acid as a probe. For example, p27$^{Kip1}$ genes can be isolated by screening a genomic or cDNA library with a p27$^{Kip1}$ nucleic acid probe. Such a probe can be, for example, a portion of a p27$^{Kip1}$ gene or its specific RNA, or a fragment thereof, that exhibits low codon degeneracy. Such a probe can be prepared, detectably labeled, and used to screen a library by nucleic acid hybridization (see, e.g., Benton and Davis, *Science* 196:180-82 (1977); Grunstein and Hogness, *Proc. Natl. Acad. Sci. USA* 72:3961-65 (1975); Sambrook et al., supra; Ausubel et al., supra). DNA fragments with substantial identity to the probe will hybridize and can be identified using the detectable label.

In various embodiments, hybridization screening using a heterologous p27$^{Kip1}$ nucleic acid probe can assist in the isolation of p27$^{Kip1}$ genes. p27$^{Kip1}$ genes can be isolated, for example, from human or non-human sources, such as, for example, primato, porcine, bovine, feline, equine, canine, ovine, avian, reptilian, amphibian, piscine, and the like; and from non-vertebrate sources, such as insects, worms, nematodes, and the like. In certain embodiments, the isolated p27$^{Kip1}$ gene can be from a chicken, goose, duck, lobster, rabbit, sheep, cow, bull, horse, pig, and the like.

By way of example, and not limitation, procedures using low stringency conditions are as follows: Filters containing DNA are pretreated for 6 hours at 40° C. in a solution containing 35% formamide, 5×SSC, 50 mM Tris-HCl (pH 7.5), 5 mM EDTA, 0.1% polyvinylpyrrolidone (PVP), 0.1% Ficoll, 1% bovine serum albumin (BSA), and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe. Filters are incubated in hybridization mixture for 18-20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65-68° C. and re-exposed to film. Other conditions of low stringency that can be used are well known in the art (e.g., those employed for cross-species hybridizations). (See also Shilo and Weinberg, *Proc. Natl. Acad. Sci. USA* 78:6789-92 (1981); Sambrook et al., supra; Ausubel et al., supra.)

Alternatively, moderate stringency conditions can be used. By way of example, and not limitation, procedures using such conditions of moderate stringency are as follows: Prehybridization of filters containing DNA is carried out for 8 hours to overnight at 55° C. in buffer composed of 6×SSC, 50 mM Tris-HCl (pH 7.5), 1 mM EDTA, 0.02% PVP, 0.2% Ficoll, 0.02% BSA and 500 µg/ml denatured salmon sperm DNA. Filters are hybridized for 24 hours at 55° C. in a prehybridization mixture containing 100 µg/ml denatured salmon sperm DNA and 5-20×10$^6$ cpm of $^{32}$P-labeled probe. Washing of filters is done at 37° C. for 1 hour in a solution containing 2×SSC, 0.01% PVP, 0.01% Ficoll, and 0.01% BSA.

By way of example, and not limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5-20×10$^6$ cpm of $^{32}$P-labeled probe. Washing of filters can be performed at 65° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which can be used are well known in the art. (See, e.g., Ausubel et al., supra; Sambrook et al., supra.)

Various other hybridization conditions can be used. For example, hybridization in 6×SSC at about 45° C., followed by washing in 2×SSC at 50° C. can be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M NaH$_2$PO$_4$ (pH7.2)/1 mM EDTA/7% SDS, or hybridization in 50% formamide/0.25M NaH$_2$PO$_4$ (pH7.2)/0.25 M NaCl/1 mM EDTA/7% SDS, followed by washing in 40 mM NaH$_2$PO$_4$ (pH7.2)/1 mM EDTA/5% SDS at 50° C. or in 40 mM NaH$_2$PO$_4$ (pH7.2)/1 mM EDTA/1% SDS at 50° C. Both temperature and salt can be varied, or alternatively, one or the other variable can remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al. (supra) and Ausubel et al. (supra).

p27$^{Kip1}$ genes can also be identified, for example, by searching a genomic sequence database, such as those for *Drosophila, C elegans*, and the like. Such searches can be performed, for example, using the Blast search engine (Altschul et al., *Nucleic Acids Res.* 25:3389-402 (1997)), or other suitable sequence comparison program. Information and tools for screening genomic databases are provided, for example, at the NCBI Internet web site (http://www.ncbi.nlm.nih.gov), as well as from commercially available sources. The UniGene collection provides a non-redundant set of sequences that represent unique genes of different sequences. (See www.ncbi.nlm.nih.gov.) This collection includes well-characterized genes, as well as thousands of expressed sequence tag (EST) sequences.

The methods discussed above are not meant to limit the methods by which p27$^{Kip1}$ genes can be isolated. p27$^{Kip1}$ genes derived frown genomic DNA can contain regulatory and intron DNA regions in addition to coding regions; clones derived from cDNA will typically contain only exon sequences. Nucleic acids can be molecularly cloned into a suitable vector for propagation of those nucleic acids. (See, e.g., Sambrook et al., supra; Ausubel et al., supra.)

A p27$^{Kip1}$ gene can be mutagenized to create a substitution, deletion and/or insertion in the Cdk2 phosphorylation site. In an exemplary embodiment, a substitution of the phosphorylated threonine or serine is made by altering the codon that codes for that residue. In other embodiments, other residues in the Cdk2 phosphorylation site can be changed or deleted. This can be accomplished, for example, by site-directed mutagenesis using the Amersham technique (Amersham mutagenesis kit, Amersham, Inc., Cleveland, Ohio) based on the methods of Taylor et al. (*Nucl. Acids Res.* 13:8749-84 (1985); *Nucl. Acids Res.* 13:8764-85 (1985)), Nakamaye and Eckstein (*Nucl Acids Res.* 14:9679-98 (1986)); and Dente et al. (*DNA Cloning*, Glover, Ed., IRL Press, pp. 791-802 (1985)); using a Promega kit (Promega Inc., Madison, Wis.); using a Biorad kit (Biorad Inc., Richmond, Calif.), based on the methods of Kunkel (*Proc. Natl. Acad. Sci. USA* 82:488-92 (1985); *Meth. Enzymol.* 154:367-82(1987); U.S. Pat. No. 4,873,192), and the like. Site directed mutagenesis can also be accomplished using PCR-based mutagenesis, such as the technique described by Zhengbin et al. (in *PCR Methods and Applications*, Cold Spring Harbor Laboratory Press, New York, pp. 205-207 (1992)), by Jones and Howard (*BioTechniques* 8:178-83 (1990); *BioTechniques* 10:62-66 (1991)); by Ho et al. (*Gene* 77:51-59 (1989)), and by Horton et al. (*BioTechniques* 8:528-35 (1990); *Gene* 77:61-68 (1989)). Other methods of mutagenizing a $p27^{Kip1}$ gene to modify a Cdk2 phosphorylation site are known to the skilled artisan and are within the scope of the invention.

A mutant $p27^{Kip1}$ gene can be part of an expression cassette, ie., having a promoter and a coding region encoding a mutant $p27^{Kip1}$ polypeptide. The promoter can be a homologous promoter (i.e., a $p27^{Kip1}$ gene promoter from the same species) or a heterologous promoter (i.e., a $p27^{Kip1}$ gene promoter from a different species, or a non-$p27^{Kip1}$ gene promoter) for expression of a mutant $p27^{Kip1}$ coding region (i.e., lacking a Cdk2 phosphorylation site). As used herein, the term "coding region" refers to a nucleotide sequence containing a translational initiation codon followed by an ordered arrangement of codons that encode a mutant $p27^{Kip1}$ protein and a translational termination codon. A "coding region" can also encode a fragment of a mutant $p27^{Kip1}$ protein lacking a Cdk2 phosphorylation site. The promoter is operably or operatively associated with the coding region, whereby the promoter effects expression of the coding region.

Suitable heterologous promoters include, for example, promoters that are expressed in a wide variety of tissue types, such as, for example, the SV40 early promoter region (Benoist and Chambon, *Nature* 290:304-10 (1981)), the promoter contained in the 3' long terminal repeat of Rous sarcoma virus (Yamamoto et al., *Cell* 22:787-97 (1980)), the herpes thymidine kinase promoter (Wagner et al., *Proc. Natl. Acad. Sci. USA* 78:1441-45 (1981)), the regulatory sequences of the metallothionein gene (Brinster et al., *Nature* 296:39-42 (1982)), the cytomegalovirus (CMV) promoter, the mouse Oct4 gene promoter (International Patent Publication No. WO 00/56932), the Mouse Moloney Leukemia Virus LTR (Miller and Buttimore, *Mol. Cell. Biol.* 6:2895-902 (1986), Gossen and Bujard, *Proc. Natl. Acad. Sci. USA* 89:5547-51 (1992); Pescini et al., *Biochem. Biophys Res. Comm.* 202: 1664-67 (1994)); ubiquitously expressed promoters such as the ROSA26 and G3BP promoters (Zambrowicz et al., *Proc. Natl. Acad. Sci. USA* 94:3789-94 (1997); Parker et al., *Molecular and Cellular Biology* 16:2561-69 (1996)); and the like.

For expression in avian species, the promoter can be, for example, lactoferrin-derived transcription regulatory sequences (International Publication No. WO 00/75300), the chicken ovalbumin promoter (Genbank Accession Nos. J00895 or M24999), the chicken lysozyme promoter (Genbank Accession Nos. J00886 or V00429), and the like. Other suitable promoters are known to those of skill in the art. In certain embodiments, an Internal Ribosomal Entry Site (IRES) can be part of a promoter system express a mutant $p27^{Kip1}$ gene. Suitable polyadenylation sequences include, for example, the human beta-globin polyadenylation sequence, and the SV40 early polyadenylation sequence.

The mutant $p27^{Kip1}$ gene expression cassette optionally can further include a selectable marker, such as a positively and/or negatively selectable marker. Suitable positively selectable markers can include, for example, the neomycin gene, the hygromycin gene, the hisD gene, the xanthine-guanine phosphoribosyltransferase (Gpt) gene conferring resistance to mycophenolic acid (Mulligan et al., *Proc. Natl. Acad. Sci. USA* 78:2072-76 (1981)), the hypoxanthine phosphoribosyl transferase (Hprt) gene, and the like. Suitable negative selection markers include, for example, the HSV thymidine kinase gene, the Hprt gene, the Gpt gene, Diphtheria toxin, Ricin toxin, cytosine deaminase, and the like. The selectable marker typically confers a phenotype for identification and isolation of cells containing an introduced mutant $p27^{Kip1}$ gene.

A mutant $p27^{Kip1}$ gene optionally can be part of an expression vector. Such an expression vector typically comprises an expression cassette (e.g., a promoter operably linked to a mutant $p27^{Kip1}$ gene operably linked to a polyadenylation sequence), one or more origins of replication, and, optionally, one or more selectable markers (e.g., an antibiotic resistance gene and/or any of those describe above). Suitable origins of replication include, for example, the SV40 origin of replication, the colE1 origin of replication, and the like.

Suitable expression vectors can include defective or attenuated retroviral vectors or other viral vector (see, e.g., U.S. Pat. No. 4,980,286). For example, a retroviral vector, as described by Miller et al. (*Meth. Enzymol.* 217:581-99 (1993)) can be used. (See also Boesen et al., *Biotherapy* 6:291-302 (1994).) (These references are incorporated herein in their entirety.) These retroviral vectors are typically modified to delete retroviral sequences that are not necessary for packaging of the viral genome and integration into host cell DNA. The mutant $p27^{Kip1}$ gene is inserted into the vector, which facilitates delivery of the gene into a cell. Lentiviral vectors can also be used. (See, e.g., Naldini et al., *Science* 272:263-67 (1996), incorporated by reference herein in its entirety.)

Adenoviruses can also be used as an expression vector to introduce a mutant $p27^{Kip1}$ gene into cells. Adenoviruses have the advantage of being capable of infecting non-dividing cells. Adeno-associated virus (AAV) are another suitable vector. (See, e.g., Ali et al., *Gene Therapy* 1:367-84 (1994); U.S. Pat. Nos. 4,797,368 and 5,139,941; Walsh et al., *Proc. Soc. Exp. Biol. Med.* 204:289-300 (1993); Grimm et al., *Human Gene Therapy* 10:2445-50 (1999); the disclosures of which are incorporated by reference herein in their entirety.)

The expression cassette or vector can be used for homologous integration of a mutant $p27^{Kip1}$ gene at a predetermined locus in the genome of a cell. For example, a mutant $p27^{Kip1}$ gene can be homologously integrated at an endogenous $p27^{Kip1}$ locus in a cell. Alternatively, a mutant $p27^{Kip1}$ gene can be integrated at any other suitable locus in a cell, such as a non-essential gene locus or other non-essential genomic region. As used herein, the term "homologous recombination" refers to a process of recombination or gene conversion whereby homology regions flanking a mutant $p27^{Kip1}$ gene, or a portion thereof (e.g. the nucleic acid sequence encoding a Cdk2 phosphorylation site), replace corresponding chromosomal sequences in the genome of the cell.

Homologous recombination can occur by, for example, double-crossover replacement recombination, in which homologous recombination (e.g., strand exchange, strand pairing, strand scission, and strand ligation) occurs between homology regions in an expression vector or expression construct and chromosomal sequences in a cell. The homology regions are generally used in the same orientation (e.g., the upstream direction (5' relative to the direction of transcription) is the same for each homology region) to avoid rearrangements. Double-crossover replacement recombination thus can be used to insert a mutant p27$^{Kip1}$ gene, or a portion thereof, into an endogenous gene locus. In certain embodiments, the homology regions are from an endogenous p27$^{Kip1}$ gene, and the mutant p27$^{Kip1}$ gene or a fragment thereof, integrates at an endogenous p27$^{Kip1}$ gene locus. Alternatively, the homologous regions are from a different locus, and the mutant p27$^{Kip1}$ gene is integrated at that locus.

Suitable "targeting constructs" for homologous integration of a mutant p27$^{Kip1}$ gene include, for example, those disclosed in U.S. Pat. Nos. 5,631,153; 5,627,059; 5,487,992; 5,464,764; and 6,204,061 (the disclosures of which are incorporated by reference herein in their entirety). Targeting constructs can be, for example, a targeting construct for single-crossover integration, or "hit-and-run" targeting, which has only a single homology region linked to a mutant p27$^{Kip1}$ gene or gene fragment. Alternatively, the targeting construct can have two homology regions, each flanking a mutant p27$^{Kip1}$ gene or gene fragment. For example, a targeting construct can comprise, in order: (1) a first homology region having a sequence substantially identical to a sequence of a portion of an endogenous gene locus, (2) a mutant p27$^{Kip1}$ gene or a fragment thereof, and (3) a second homology region having a sequence substantially identical to a different portion of the endogenous gene locus. In certain embodiments, the targeting construct further comprises a negatively selectable marker (e.g., Diphtheria toxin gene with the PGK promoter driving transcription) linked to an outer end of a homology region. Such a targeting construct can optionally further include a positively selectable marker disposed between the first and second homology regions. The homology regions typically range from between about 50 base pairs to about several tens of kilobases. In some embodiments, targeting constructs are generally at least about 250 nucleotides, at least about 500 nucleotides, typically at least about 1000 to about 6000 nucleotides, or longer.

The homology region(s) can be selected at the discretion of the practitioner on the basis of the sequence composition and complexity of the gene locus and guidance provided in the art (see, e.g., Hasty et al., *Mol. Cell. Biol.* 11:5586-91 (1991); Shulman et al., *Mol. Cell. Biol.* 10:4466-72 (1990), which are incorporated herein by reference in their entirety). Targeting constructs are generally double-stranded DNA molecules; most are typically linear. General principles regarding the construction of targeting constructs and selection methods are reviewed in Bradley et al. (*Bio/Technology* 10:534-39 (1992), incorporated herein by reference in its entirety). (See also Capecchi, *Science* 244:1288-92 (1989); incorporated herein by reference in its entirety.)

In another aspect, transgenic cells comprising one or more mutant p27$^{Kip1}$ genes are provided. As used herein, the term "transgenic cells" refers to a human or non-human cell comprising one or more mutant p27$^{Kip1}$ genes. A transgenic cells can be, for example, from a human, primate, mammal, avian, porcine, ovine, bovine, feline, canine, fowl, rodent, fish, crustacean, and the like. In specific embodiments, the transgenic cells can be from a sheep, goat, horse, cow, bull, pig, rabbit, guinea pig, hamster, rat, gerbil, mouse, chicken, ostrich, emu, turkey, duck, goose, quail, parrot, parakeet, cockatoo, cockatiel, trout, cod, salmon, crab, king crab, lobster, or shrimp.

Mutant p27$^{Kip1}$ genes can be introduced into target cells, such as, for example, pluripotent or totipotent cells such as embryonic stem (ES) cells (e.g., murine embryonal stem cells or human embryonic stem cells) or other stem cells (e.g., adult stem cells); germ cells (e.g., primordial germ cells, oocytes, eggs, spermatocytes, or sperm cells); fertilized eggs; fetal or adult somatic cells, either differentiated or undifferentiated (e.g., thymocytes, fibroblasts, keratinocytes, brain, muscle, liver, lung, bone marrow, heart, neuron, gastrointestinal, kidney, spleen, or epithelial cells); and the like. In certain embodiments, the mutant p27$^{Kip1}$ gene can be introduced into embryonic stem cells or germ cells.

Suitable transgenic cells can also include "cell lines," which refers to individual cells, harvested cells, and cultures containing the cells derived from cells of the cell line referred to. A cell line is said to be "continuous," "immortal," or "stable" if the line remains viable over a prolonged time, typically at least about six months. Suitable transgenic cells can also include primary cells. Primary cells include cells that are obtained directly from an organism or that are present within an organism, and cells that are obtained from these sources and grown in culture, but are not capable of continuous (e.g., many generations) growth in culture. For example, primary fibroblast cells are considered primary cells. Cells can be modified in vitro, ex vivo, or in vivo.

In a related aspect, transgenic animals harboring one or more mutant p27$^{Kip1}$ genes, and methods of making such animals, are provided. As used herein, the term "transgenic animal" refers to a non-human animal that harbors cells containing one or more mutant p27$^{Kip1}$ genes. A transgenic animal can be, for example, a primate, mammal, avian, porcine, ovine, bovine, feline, canine, fowl, rodent, fish, crustacean, and the like. In specific embodiments, the transgenic animal can be a sheep, goat, horse, cow, bull, pig, rabbit, guinea pig, hamster, rat, gerbil mouse, chicken, ostrich, emu, turkey, duck, goose, quail, parrot, parakeet, cockatoo, cockatiel, trout, cod, salmon, crab, king crab, lobster, or shrimp. Transgenic animals include chimeric animals (i.e., those composed of a mixture of genetically different cells), mosaic animals (i.e., an animal composed of two or more cell lines of different genetic origin or chromosomal constitution, both cell lines derived from the same zygote), immature animals, fetuses, blastulas, and the like.

In mutant p27$^{Kip1}$ transgenic animals, the mutant p27$^{Kip1}$ gene causes an increased size of at least a portion of the animal, as compared with wild-type, non-transgenic animal (i.e., not having a mutant p27$^{Kip1}$ gene). In certain embodiments, the mutant p27$^{Kip1}$ transgenic animals have enlarged tissues that contain more cells or larger cells than tissues from a non-transgenic animal. In other embodiments, mutant p27$^{Kip1}$ animals exhibit increased female fertility, reduced pituitary tumorigenesis, and reduced retinal architecture disruption, as compared with animals having p27$^{Kip1}$ gene disruption(s) or knockout(s) (i.e., loss of p27$^{Kip1}$ function). Transgenic animals can contain one or more mutant p27$^{Kip1}$ genes at the endogenous p27$^{Kip1}$ locus, and/or at a non-p27$^{Kip1}$ locus (or loci). The transgenic animals can be homozygous or heterozygous for the mutant p27$^{Kip1}$ gene.

Transgenic, non-human animals containing a mutant p27$^{Kip1}$ gene can be prepared by methods known in the art. In general, a mutant p27$^{Kip1}$ gene is introduced into target cells, which are then used to prepare a transgenic animal. Mutant p27$^{Kip1}$ genes can be introduced into target cells, such as for example, pluripotent or totipotent cells such as embryonic stem (ES) cells (e.g., murine embryonal stem cells or human embryonic stem cells) or other stem cells (e.g., adult stem cells); germ cells (e.g., primordial germ cells, oocytes, eggs, spermatocytes, or sperm cells); fertilized eggs; zygotes; blastomeres; and the like; fetal or adult somatic cells (either differentiated or undifferentiated); and the like. In certain embodiments, the mutant p27$^{Kip1}$ gene can be introduced into embryonic stem cells or germ cells of animals (e.g., mammals, farm animals, livestock, hatchery animals, and the like) to prepare a mutant p27$^{Kip1}$ transgenic animal.

Embryonic stem cells can be manipulated according to published procedures (see, e.g., *Teratocarcinomas and Embryonic Stem Cells: A Practical Approach*, Robertson (ed.), IRL Press, Washington, D.C. (1987); Zjilstra et al., *Nature* 342:435-38 (1989); Schwartzberg et al., *Science* 246: 799-803 (1989); U.S. Pat. Nos. 6,194,635; 6,107,543; and 5,994,619; each of which is incorporated herein by reference in their entirety). Methods for isolating primordial germ cells are well known in the art. For example, methods of isolating primordial germ cells from ungulates are disclosed in U.S. Pat. No. 6,194,635 (the disclosure of which is incorporated by reference herein in its entirety). Briefly, primordial germ cells are isolated from gonadal ridges of an embryo at a particular stage in development (e.g., day-25 porcine embryos or day 34-40 bovine embryos). The stage of development at which primordial germ cells are extracted from an embryo of a particular species will vary with the species, as will be appreciated by the skilled artisan. Determination of the appropriate embryonic developmental stage for such extraction is readily performed using the guidance provided herein and ordinary skill in the art.

Primordial germ cells can be isolated from the dorsal mesentery and usually test positive for alkaline phosphate activity. The cells can be isolated at a suitable time after fertilization. To ascertain that harvested cells are of an appropriate developmental age, harvested cells can be tested for morphological criteria which can be used to identify primordial germ cells which are pluripotent (see, e.g., DeFelici and McLaren, *Exp. Cell Res.* 142:476-82 (1982)). To further substantiate pluripotency, a sample of the extracted cells can be subsequently tested for alkaline phosphatase (AP) activity. Pluripotent cells, such as primordial germ cells, can share markers typically found on stem cells. Primordial or embryonic germ cells typically manifest alkaline phosphatase (AP) activity, and AP positive cells are typically germ cells. AP activity is rapidly lost with differentiation of embryonic germ cells in vitro. Expression of AP also has been demonstrated in ES and ES-like cells in the mouse (see, e.g., Wobus et al., *Exp. Cell. Res.* 152:212-19 (1984); Pease et al., *Dev. Bio.* 141:344-52 (1990)), rat (see, e.g., Ouhibi et al., *Mol. Repro. Dev.* 40:311-24 (1995)), pig (see, e.g., Talbot et al., *Mol. Repro. Dev.* 36:139-47 (1993)) and bovine animals (see, e.g., Talbot et al., *Mol. Repro. Dev.* 42:35-52 (1995)). AP activity has also been detected in murine primordial germ cell (see, e.g., Chiquoine, *Anat. Rec.* 118:135-46 (1954)), murine embryonic germ cells (see, e.g., Matsui et al., *Cell* 70:84147 (1992); Resnick et al., *Nature* 359:550-51 (1992)) and porcine primordial germ cells.

In a particular embodiment, transgenic avian animals can be prepared using avian primordial germ cells. Such methods are disclosed, for example, in U.S. Pat. No. 5,156,569 (the disclosure of which is incorporated by reference herein in its entirety). Generally, primordial germ cells are isolated and cultured in the presence of growth factors, such as, for example, leukemia inhibiting factor (LIF), stem cell factor (SCF), insulin-like growth factor (IGF) and/or basic fibroblast growth factor (bFGF).

Methods for isolation of primordial germ cells from donor avian embryos have been reported in the literature and can be effected by one skilled in the art. (See, e.g., JP 924997 (Pub. No. 05-227947); Chang et al., *Cell Biol. Int.* 19:143-49 (1992); Naito et al., *Mol. Reprod. Devel.* 39:153-61 (1994); Yasuda et al., *J. Reprod. Fert.* 96:521-28 (1992); Chang et al., *Cell Biol. Int. Reporter* 16:853-57 (1992); each of which is incorporated by reference in their entirety therein.) In one example, primordial germ cells are isolated from chicken eggs which have been incubated for about 53 hours (stage 12-14 of embryonic development), embryos are removed, embryonic cells are collected from the dorsal aorta thereof, and transferred to suitable cell culture medium (e.g., M199 medium). These primordial germ cells can be purified (e.g., by Ficoll density centrifugation) and resuspended in growth factor-containing culture medium. The isolated primordial germ cells are then counted and separated manually (e.g., using a pipette). To increase the number of primordial germ cells, cells can be collected from multiple avian embryos and pooled. The isolated primordial germ cells can be incubated in a suitable growth factor-containing medium. For example, one suitable culture medium includes α-MEM, containing 10% fetal calf serum, 2 mM L-glutamine, 0.56% antibiotic/antimitotic, 34.56 mM β-mercaptoethanol, 0.00625 U/µl of LIF, 0.25 pg/µl of bFGF, 0.5625 pg/µl of IGF and 4.0 pg/µl of SCF.

Mutant $p27^{Kip1}$ genes can be introduced into target cells by any suitable method. For example, a mutant $p27^{Kip1}$ gene(s) can be introduced into a cell by transfection (e.g. calcium phosphate or DEAE-dextran mediated transfection), lipofection, electroporation, microinjection (e.g., by direct injection of naked DNA), biolistics, infection with a viral vector containing a mutant $p27^{Kip1}$ gene, cell fusion, chromosome-mediated gene transfer, microcell-mediated gene transfer, nuclear transfer, and the like.

In certain embodiments, a mutant $p27^{Kip1}$ gene is introduced into target cells by transfection or lipofection. Suitable agents for transfection or lipofection include, for example, calcium phosphate, DEAE dextran, lipofectin, lipfectamine, DIMRIE C, Superfect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, poly(ethylenimine) (PEI), and the like. (See, e.g., Banerjee et al., *Med. Chem.* 42:4292-99 (1999); Godbey et al., *Gene Ther.* 6:1380-88 (1999); Kichler et al., *Gene Ther.* 5:855-60 (1998); Birchaa et al., *J. Pharm.* 183:195-207 (1999); each incorporated by reference herein in its entirety.)

For avian species, which form a shell, the optimal time to introduce a mutant $p27^{Kip1}$ gene, into avian cells is after oviposition and within six hours of activation (post-incubation) so that the cells have started to grow but have not undergone a cell division. Oviposition is the time at which the egg is laid. In the chicken, oviposition typically occurs at about 20 hours of uterine age. Mutant $p27^{Kip1}$ genes can be introduced into the blastoderm or germinal disc after oviposition, but before incubation of the egg (i.e., before the first cell division after the egg is incubated). The germinal disc is distinguished from the germinal crescent region in that the germinal disc contains undifferentiated blastodermal cells, whereas the germinal crescent region appears in the early stages of chick embryo development.

In certain embodiments, the blastoderm is accessed by cutting or drilling a small hole in the egg shell (sitting upright) with a scalpel or drill and gently peeling back the inner membrane to expose the white albumen. The blastoderm orients to the top of the yolk and is visualized under light. The cells of the blastoderm can be transfected in vivo by infusing nucleic acids (e.g., DNA) directly into the blastoderm using a syringe and small gauge needle. The nucleic acid can be naked or complexed with lipids or other suitable compounds to facilitate DNA uptake (e.g., DEAE-dextran). If the DNA is naked, the transfection efficiency can be increased by passing an electrical current across the blastoderm or whole egg with a device, such as a human heart defibrillator. If a current is passed across the whole egg, two additional holes are made in the egg shell to expose the inner membrane to the current since the shell will not conduct electricity.

Alternatively, the blastoderm can be removed from the egg and pooled with cells from several eggs (e.g., using a small pipet). In vitro, nucleic acid uptake by blastodermal cells is facilitated by such techniques as electroporation, DEAE-dextran treatment, calcium phosphate treatment, lipofection, and the like. Following transfection, the cells can be transferred into the germinal disc of an unfertilized egg for development of a transgenic chick.

The overall efficiency of the nucleic acid delivery procedure to avian cells can depend on the methods and timing of gene delivery. Transfection efficiency is optionally increased by, for example, subjecting the blastoderm or cells derived from the blastoderm to several rounds of transfection or adding a selectable marker to the mutant p27$^{Kip1}$ gene and infusing antibiotic, or other suitable drug, into the yolk or testes following transfection or cell transfer.

The mutant p27$^{Kip1}$ genes also can be introduced into cells by electroporation (see, e.g., Wong and Neumann, *Biochem. Biophys. Res. Commun.* 107:584-87 (1982)) and biolistics (e.g., a gene gun; Johnston and Tang, *Methods Cell Biol.* 43 Pt A:353-65 (1994); Fynan et al., *Proc. Natl. Acad. Sci. USA* 90:11478-82 (1993)).

Methods of introducing mutant p27$^{Kip1}$ genes into target cells further include microinjection of the gene into target cells. For example, a mutant p27$^{Kip1}$ gene can be microinjected into pronuclei of fertilized oocytes or the nuclei of ES cells. A typical method is microinjection of the fertilized oocyte. The fertilized oocytes are microinjected with nucleic acids encoding mutant p27$^{Kip1}$ genes by standard techniques. The microinjected oocytes are typically cultured in vitro until a "pre-implantation embryo" is obtained. Such a pre-implantation embryo typically contains approximately 16 to 150 cells. The 16 to 32 cell stage of an embryo is commonly referred to as a "morula." Those pre-implantation embryos containing more than 32 cells are commonly referred to as "blastocysts." They are generally characterized as demonstrating the development of a blastocoel cavity typically at the 64 cell stage. Methods for culturing fertilized oocytes to the pre-implantation stage include those described by Gordon et al. (*Methods in Enzymology* 101:414 (1984)); Hogan et al. (in *Manipulating the Mouse Embryo*, Cold Spring Harbor Laboratory Press, Cold Spring Harbor, N.Y. (1986)); Hammer et al. (*Nature* 315:680 (1986)); Gandolfi et al. (*J. Reprod. Fert.* 81:23-28 (1987)); Rexroad et al. (*J. Anim. Sci.* 66:947-53 (1988)); Eyestone et al. (*J. Reprod. Fert.* 85:715-20 (1989)); Camous et al. (*J. Reprod. Fert.* 72:779-85 (1989)); and Heyman et al. (*Theriogenology* 27:5968 (1989)) for mice, rabbits, pigs, cows, and the like. (These references are incorporated herein in their entirety.) Such pre-implantation embryos can be thereafter transferred to an appropriate (e.g., pseudopregnant) female by standard methods. Depending upon the stage of development when the mutant p27$^{Kip1}$ gene, or the mutant p27$^{Kip1}$ gene-containing cell is introduced into the embryo, a chimeric or mosaic animal can result. As is well known, mosaic and chimeric animals can be bred to form true germline mutant p27$^{Kip1}$ transgenic animals by selective breeding methods well-known in the art. Alternatively, microinjected or transfected embryonic stem cells can be injected into appropriate blastocysts and then the blastocysts are implanted into the appropriate foster females (e.g., pseudopregnant females).

A mutant p27$^{Kip1}$ gene also can be introduced into cells by infection of cells or into cells of a zygote with an infectious virus containing the mutant gene. Suitable viruses include retroviruses (see generally Jaenisch, *Proc. Natl. Acad. Sci. USA* 73:1260-64 (1976)); defective or attenuated retroviral vectors (see, e.g., U.S. Pat. No. 4,980,286; Miller et al., *Meth. Enzymol.* 217:581-99 (1993); Boesen et al., *Biotherapy* 6:291-302 (1994); these references are incorporated herein in their entirety), lentiviral vectors (see, e.g., Naldini et al., *Science* 272:263-67 (1996), incorporated by reference herein in its entirety), adenoviruses or adeno-associated virus (AAV) (see, e.g., Ali et al., *Gene Therapy* 1:367-84 (1994); U.S. Pat. Nos. 4,797,368 and 5,139,941; Walsh et al., *Proc. Soc. Exp. Biol. Med.* 204:289-300 (1993); Grimm et al., *Human Gene Therapy* 10:2445-50 (1999); the disclosures of which are incorporated by reference herein in their entirety).

Viral vectors can be introduced into, for example, embryonic stem cells, primordial germ cells, oocytes, eggs, spermatocytes, sperm cells, fertilized eggs, zygotes, blastomeres, or any other suitable target cell. In an exemplary embodiment, retroviral vectors which transduce dividing cells (e.g., vectors derived from murine leukemia virus; see, e.g. Miller and Baltimore, *Mol. Cell. Biol.* 6:2895 (1986)) can be used. The production of a recombinant retroviral vector carrying a gene of interest is typically achieved in two stages. First, a mutant p27$^{Kip1}$ gene can be inserted into a retroviral vector which contains the sequences necessary for the efficient expression of the mutant p27$^{Kip1}$ gene (including promoter and/or enhancer elements which can be provided by the viral long terminal repeats (LTRs) or by an internal promoter/enhancer and relevant splicing signals), sequences required for the efficient packaging of the viral RNA into infectious virions (e.g., a packaging signal (Psi), a tRNA primer binding site (−PBS), a 3' regulatory sequence required for reverse transcription (+PBS)), and a viral LTRs). The LTRs contain sequences required for the association of viral genomic RNA, reverse transcriptase and integrase functions, and sequences involved in directing the expression of the genomic RNA to be packaged in viral particles.

Following the construction of the recombinant vector, the vector DNA is introduced into a packaging cell line. Packaging cell lines provide viral proteins required in trans for the packaging of viral genomic RNA into viral particles having the desired host range (i.e., the viral-encoded core (gag), polymerase (pol) and envelope (env) proteins). The host range is controlled, in part, by the type of envelope gene product expressed on the surface of the viral particle. Packaging cell lines can express ecotrophic, amphotropic or xenotropic envelope gene products. Alternatively, the packaging cell line can lack sequences encoding a viral envelope (env) protein. In this case, the packaging cell line can package the viral genome into particles which lack a membrane-associated protein (e.g., an env protein). To produce viral particles containing a membrane-associated protein which permit entry of the virus into a cell, the packaging cell line containing the retroviral sequences can be transfected with sequences encoding a membrane-associated protein (e.g., the G protein of vesicular stomatitis virus (VSV)). The transfected packaging cell can then produce viral particles which contain the membrane-associated protein expressed by the transfected packaging cell line; these viral particles which contain viral genomic RNA derived from one virus encapsidated by the envelope proteins of another virus are said to be pseudotyped virus particles.

Oocytes which have not undergone the final stages of gametogenesis are typically infected with the retroviral vector. The injected oocytes are then permitted to complete maturation with the accompanying meiotic divisions. The breakdown of the nuclear envelope during meiosis permits the integration of the proviral form of the retrovirus vector into the genome of the oocyte. When pre-maturation oocytes are used, the injected oocytes are then cultured in vitro under conditions that permit maturation of the oocyte prior to fertilization in vitro. Conditions for the maturation of oocytes from a number of mammalian species (e.g., bovine, ovine, porcine, murine, and caprine) are well known in the art. In general, a base medium for in vitro maturation of bovine oocytes can be used (e.g. TC-M199 medium supplemented with hormones (e.g., luteinizing hormone and estradiol)). Other media for the maturation of oocytes can be used for the in vitro maturation of other mammalian oocytes and are well known to the skilled artisan. The amount of time a pre-maturation oocyte is exposed to maturation medium to permit maturation varies between mammalian species, as is known to the skilled artisan. For example, an exposure of about 24 hours is sufficient to permit maturation of bovine oocytes, while porcine oocytes require about 44-48 hours.

Oocytes can be matured in vivo and employed in place of oocytes matured in vitro. For example, when porcine oocytes are employed, matured pre-fertilization oocytes can be harvested directly from pigs that are induced to superovulate. Briefly, on day 15 or 16 of estrus, a female pig(s) can be injected with about 1000 units of pregnant mare's serum (PMS; available from Sigma and Calbiochem). Approximately 48 hours later, the pig(s) is injected with about 1000 units of human chorionic gonadotropin (hCG; Sigma), and 24-48 hours later matured oocytes are collected from oviduct. These in vivo matured pre-fertilization oocytes can then be injected with the desired preparation. Methods for the superovulation and collection of in vivo matured (e.g., oocytes at the metaphase 2 stage) oocytes are known for a variety of mammals (e.g., for superovulation of mice, see Hogan et al., in *Manipulating the Mouse Embryo: A Laboratory Manual,* 2nd ed., Cold Spring Harbor Laboratory Press, Cold Spring Harbor, N.Y. (1994), pp. 130-133; the disclosure of which is incorporated by reference herein in its entirety).

Retroviral vectors capable of infecting the desired species of non-human animal can be grown and concentrated to very high titers (e.g., $1 \times 10^8$ cfu/ml). The use of high titer virus stocks allows the introduction of a defined number of viral particles into the perivitelline space of each injected oocyte. The perivitelline space of most mammalian oocytes can accommodate about 10 picoliters of injected fluid (those skilled in the art know that the volume that can be injected into the perivitelline space of a mammalian oocyte or zygote varies somewhat between species as the volume of an oocyte is smaller than that of a zygote and thus, oocytes can accommodate somewhat less than can zygotes). The virus stock can be titered and diluted prior to microinjection into the perivitelline space so that the number of proviruses integrated in the resulting transgenic animal is controlled. The use of pre-maturation oocytes or mature fertilized oocytes as the recipient of the virus minimizes the production of animals which are mosaic for the provirus as the virus integrates into the genome of the oocyte prior to the occurrence of cell cleavage.

Prior to microinjection of the titered and diluted (if required) virus stock, the cumulus cell layer can be opened to provide access to the perivitelline space. The cumulus cell layer need not be completely removed from the oocyte and indeed for certain species of animals (e.g., cows, sheep, pigs, or mice), a portion of the cumulus cell layer remains in contact with the oocyte to permit proper development and fertilization post-injection. Injection of viral particles into the perivitelline space allows the vector RNA (i.e., the viral genome) to enter the cell through the plasma membrane thereby allowing proper reverse transcription of the viral RNA. The presence of the retroviral genome in cells (e.g., oocytes or embryos) infected with pseudotyped retrovirus can be detected using a variety of means, such as those d described herein or as otherwise known to the skilled artisan.

In an exemplary embodiment, the mutant $p27^{Kip1}$ gene can be introduced into avian species using a viral vector as described in U.S. Pat. No. 5,162,215 (the disclosure of which is incorporated by reference herein in its entirety). Briefly, a vector, such as a retroviral vector, is used to introduce a mutant $p27^{Kip1}$ gene into cells of an avian embryo, such as a chicken. In one embodiment, a mutant $p27^{Kip1}$ viral vector is microinjected in a newly laid chicken egg arrested at stage X (not generally more than seven days old, unincubated), in close proximity to (e.g., directly underneath) the blastoderm. More specifically, an opening about 5 mm in diameter is made in the side of the egg, normally by the use of a drilling tool fitted with an abrasive rotating tip which can drill a hole in the egg shell without damaging the underlying shell membrane. The membrane is then cut out by use of a scalpel or 18 gauge needle and thumb forceps, so that a portion of the shell and membrane is removed, thereby exposing the embryo. The embryo is visualized by eye or with an optical dissecting microscope (e.g., having 6×-50× magnification). A solution, usually tissue culture medium, containing the mutant $p27^{Kip1}$ gene expression vector, is microinjected into an area beneath and around the blastoderm, using a micro-manipulator and a very small diameter needle (e.g., glass needle about 40-60 µM outer diameter at the tip, 1 mm outer diameter along its length). The volume of solution for microinjection is typically about 5-20 µl. After microinjection, the egg is sealed with shell membrane and a sealing material, such as glue or paraffin. The sealed egg can then be incubated at approximately 38° C. for various time periods up to and including the time of hatching to allow normal embryo growth and development. DNA from embryos and from newly hatched chicks can be tested for the presence of the mutant $p27^{Kip1}$ gene. The presence of the mutant $p27^{Kip1}$ gene can be detected by means known in the art and appropriate to the detection of a mutant $p27^{Kip1}$ gene or gene product.

Alternatively, a mutant $p27^{Kip1}$ gene expression vector or transfected cells producing the expression vector (e.g., a virus containing the mutant $p27^{Kip1}$ gene) is injected into developing avian oocytes in vivo, for example, as described in Shuman and Shoffner (*Poultry Science* 65:1437-44 (1986), which is incorporated by reference herein in its entirety).

The overall efficiency of the nucleic acid delivery procedure to avian cells can depend on the methods and timing of gene delivery. Infection efficiency is optionally increased by, for example, subjecting the blastoderm or cells derived from the blastoderm to several rounds of infection or adding a selectable marker to the mutant $p27^{Kip1}$ gene and infusing the antibiotic into the yolk or testes following transfection or cell transfer.

In another embodiment, a transgenic animal is prepared by nuclear transfer. The terms "nuclear transfer" or "nuclear transplantation" refer to methods of preparing transgenic animals wherein the nucleus from a donor cell is transplanted into an enucleated oocyte. Nuclear transfer techniques or nuclear transplantation techniques are known in the art. (See, e.g., Campbell et al., *Theriogenology* 43:181 (1995); Collas and Barnes, *Mol. Reprod. Dev.* 38:264-67 (1994); Keefer et al., *Biol. Reprod.* 50:935-39 (1994); Sims et al., *Proc. Natl. Acad. Sci. USA* 90:6143-47 (1993); Prather et al., *Biol. Reprod.* 37:59-86 (1988); Roble et al., *J. Anim. Sci.* 64:642-64 (1987); International Patent Publications WO 90/03432, WO 94/24274, and WO 94/26884; U.S. Pat. Nos. 4,994,384 and 5,057,420; the disclosures of which are incorporated by reference herein in their entirety.) For example, nuclei of transgenic embryos, pluripotent cells, totipotent cells, embryonic stem cells, germ cells, fetal cells or adult cells can be transplanted into enucleated oocytes, each of which is thereafter cultured to the blastocyst stage. (As used herein, the term "enucleated" refers to cells from which the nucleus has been removed as well as to cells in which the nucleus has been rendered functionally inactive.) The nucleus containing a mutant $p27^{Kip1}$ gene can be introduced into these cells by any method known to the skilled artisan, including those described herein. The transgenic cell is then typically cultured in vitro to the form a pre-implantation embryo, which can be implanted in a suitable female (e.g., a pseudo-pregnant female).

The transgenic embryos optionally can be subjected, or resubjected, to another round of nuclear transplantation. Additional rounds of nuclear transplantation cloning can be useful when the original transferred nucleus is from an adult cell (i.e., fibroblasts or other highly or terminally differentiated cell) to produce healthy transgenic animals.

Other methods for producing a mutant $p27^{Kip1}$ animal include methods adapted to use male sperm cells to carry the mutant $p27^{Kip1}$ gene to an egg. In one example, a mutant $p27^{Kip1}$ gene can be administered to a male animal's testis in vivo by direct delivery. The mutant $p27^{Kip1}$ gene can be introduced into the seminiferous tubules, into the rete testis, into the vas efferens or vasa efferentia, using, for example, a micropipette. To ensure a steady infusion of the gene delivery mixture, the injection can be made through the micropipette with the aid of a picopump delivering a precise measured volume under controlled amounts of pressure.

The micropipette is made of a suitable material, such as metal or glass, and is usually made from glass tubing which has been drawn to a fine bore at its working tip. The tip can be angulated in a convenient manner to facilitate its entry into the testicular tubule system. Also, the micropipette can be provided with a beveled working end to allow a better and less damaging penetration of the fine tubules at the injection site. The diameter of the pipette tip is typically about 15 to 45 microns, although other sizes can be used, as needed, depending on the animal's size. The tip of the pipette can be introduced into the rete testis or the tubule system of the testicle with the aid of a binocular microscope with coaxial illumination, with care taken not to damage the wall of the tubule opposite the injection point, and keeping trauma to a minimum. A small amount of a suitable, non-toxic dye can optionally be added to the gene delivery mixture (fluid) to confirm delivery and dissemination to the seminiferous tubules of the testis. In this manner, the gene delivery mixture reaches and is brought into intimate contact with the male germ cells. Suitable male germ cells include spermatozoa (e.g., male gametes) and developmental precursors thereof.

Alternatively, the mutant $p27^{Kip1}$ gene can, be introduced ex vivo into the genome of male germ cells. A number of known gene delivery methods can be used for the uptake of nucleic acid sequences into the cell. Suitable methods for introducing mutant $p27^{Kip1}$ genes into male germ cells include, for example, liposomes, retroviral vectors, adenoviral vectors, adenovirus-enhanced gene delivery systems, or combinations thereof. Whether introduced in vivo or in vitro, the mutant $p27^{Kip1}$ gene, once in contact with the male germ cells, is taken up and transported into the appropriate cell location for integration into the genome and expression.

For ex vivo introduction of a mutant $p27^{Kip1}$ gene into the genome of an animal, male germ cells are typically obtained or collected from the donor male animal by means known in the art. The germ cells are then exposed to the mutant $p27^{Kip1}$ genes. In one exemplary embodiment, male germ cells are obtained from a donor animal by transection of the testes. Transection of the isolated testicular tissue can be accomplished, for example, by isolation of the animal's testes, decapsulation, teasing apart and mincing of the seminiferous tubules. The separated cells can then be incubated in an enzyme mixture comprising enzymes to gently break up the tissue matrix and release undamaged cells such as, for example, pancreatic trypsin, collagenase type I, pancreatic DNase type I, as well as bovine serum albumin, in a modified DMEM medium. The cells can be incubated in the enzyme mixture for a period of about 5 minutes to about 30 minutes, more typically about 15 minutes to about 20 minutes, at a temperature of about 33° C. to about 37° C. After washing the cells free of the enzyme mixture, they can be placed in an incubation medium, such as DMEM, and plated on a culture dish for exposure to mutant $p27^{Kip1}$ genes.

A typical method of isolating or selecting male germ cell populations comprises obtaining specific male germ cell populations, such as spermatogonia, from a mixed population of testicular cells by extruding the cells from the seminiferous tubules and gentle enzymatic disaggregation. The spermatogonia or other male germ cell populations can be isolated from a mixed cell population by a method including the utilization of a promoter sequence, which is specifically or selectively active in cycling male germ line stem cell populations, as disclosed in International Patent Publication WO 0069257 (the disclosure of which is incorporated by reference herein in its entirety).

After transfer to the testes of a male animal, further selection can be preformed after biopsy of one or both of the recipient male's testes, or after examination of the animal's ejaculate to confirm whether the mutant $p27^{Kip1}$ gene was incorporated (e.g., by the polymerase chain reaction). The initial gene delivery can optionally include a positively selectable marker, such as a gene encoding the Green Fluorescent Protein, enhanced Green Fluorescent Protein (EGFP), Yellow Fluorescent Protein, Blue Fluorescent Protein, a phycobiliprotein, such as phycoerythrin or phycocyanin, or any other selectable marker which fluoresces under light of suitable wave-lengths, or encoding a light-emitting protein, or is other detectable.

In certain embodiments, the male germ cells containing a mutant $p27^{Kip1}$ gene can be introduced into one or more of the testes of the recipient male vertebrate after the testes of the recipient animal are depopulated of native germ cells. Substantial depopulation of the endogenous male germ cells facilitates the colonization of the recipient testis by the mutant $p27^{Kip1}$ germ cells. Depopulation of the testes can be done by any suitable means, including, for example, by gamma irradiation, by chemical treatment, by means of infectious agents such as viruses, by autoimmune depletion, or by combinations thereof. In certain embodiments, the testes are depopulated by combined treatment with an alkylating agent and gamma irradiation. The alkylating agent can be, for example, busulfan (1,4-butanediol dimethanesulphonate; Myleran, Glaxo Wellcome), chlorambucil, cyclophosphamide, melphalan, or ethyl ethanesulfonic acid, combined with gamma irradiation. A typical dose of alkylating agent is about 4 to 10 milligrams per kilogram of body weight. (See, e.g., International Patent Publication WO 00/69257, the disclosure of which is incorporated by reference herein in its entirety.) The alkylating agent can be administered by any pharmaceutically acceptable delivery system, including but not limited to, intraperitoneal, intravenous, or intramuscular injection, intravenous drip, implantation, transdermal or transmucosal delivery systems. The recipient animal can be gamma irradiated with a dose, for example, of about 200 to about 800 Rads, or about 350 to 450 Rads, directed locally to the testis to be depopulated.

During depopulation, the basic rigid architecture of the gonad is usually not destroyed, nor badly damaged. If there is disruption of the fine system of tubule formation, it can be difficult for the exogenous spermatogonia to repopulate the testis. Disruption of tubules might also lead to impaired transport of testicular sperm and result in infertility. Any controlled testicular injury of this kind is usually limited so that the Sertoli cells are not irreversibly damaged, as they are needed to provide a base for development of the germ cells during maturation. Moreover, they may play a role in preventing the host immune defense system from destroying grafted foreign spermatogonia.

Transferring the treated gem cells into the recipient testis can be accomplished by direct injection using a suitable micropipette. Support cells, such as Leydig or Sertoli cells that provide hormonal stimulus to spermatogonial differentiation, can be transferred to a recipient testis along with the modified germ cells. These transferred support cells can be autologous or heterologous to either the donor or recipient testis. A suitable concentration of cells in the transfer fluid can easily be established by simple experimentation, and in certain embodiments can be within the range of about $1\times10^5$ to about $1\times10^6$ cells per 10 µt of fluid. These cells can be introduced into the vasa efferentia, the rete testis or the seminiferous tubules, optionally with the aid of a picopump to control pressure and/or volume. Alternatively, the delivery can be performed manually. The micropipette employed is in most respects similar to that used for the in vivo injection (as described supra), except that its tip diameter generally will be about 45 to about 70 microns.

Alternatively, for avian transgenic animals, the testes can be repopulated by using blastoderm removed from an avian egg. The blastoderm cells can be pooled with cells from several eggs, as needed. In vitro, nucleic acid uptake by blastodermal cells can be facilitated by such techniques as electroporation, DEAE-dextran treatment, calcium phosphate treatment, lipofection, and the like. Following transfection, the cells can be transferred into the testes of a rooster (e.g., a sterile rooster) to induce development in spermatogonia and sperm for breeding.

The present invention also provides animal semen containing a plurality of male mutant $p27^{Kip1}$ germ cells, which is useful for breeding or other suitable purposes. The semen is obtained from ejaculate produced by mutant $p27^{Kip1}$ transgenic male animals or their transgenic male progeny (either immediate progeny or progeny separated by one or more generations). Methods of inducing ejaculation by a male animal and capturing the semen are well known. The semen can be processed (e.g., by washing, and/or stored) by means such as are known in the art. For example, storage conditions include the use of cryopreservation using programmed freezing methods and/or the use of cryoprotectants, such as, for example, dimethyl sulfoxide (DMSO), glycerol, trehalose, or propanediol-sucrose, and storage in substances such as liquid nitrogen. Cryopreservation is useful for transport of gametes as frozen germ cells. Such transport can facilitate the establishment of various valued livestock, fowl lines, and the like, at a remote distance from the donor animal.

Following transfer of a mutant $p27^{Kip1}$ gene to male germ cells by any suitable method, a transgenic zygote can be formed by breeding the male animal with a female animal. The transgenic zygote can be formed, for example, by natural mating (e.g., copulation by the male and female vertebrates of the same species), or by in vitro or in vivo artificial means. Suitable artificial means include, but are not limited to, artificial insemination, in vitro fertilization (IVF) and/or other artificial reproductive technologies, such as intracytoplasmic sperm injection (ICSI), subzonal insemination (SUZI), partial zona dissection (PZD), and the like, as will be appreciated by the skilled artisan. (See, e.g., International Patent Publication WO 00/09674, the disclosure of which is incorporated by reference herein in its entirety.)

A variety of methods can be used to detect the presence of mutant $p27^{Kip1}$ genes in target cells and/or transgenic animals. Since the frequency of transgene incorporation (i.e., mutant $p27^{Kip1}$ gene) can be low, although reliable, the detection of transgene integration in the pre-implantation embryo can be desirable. In one aspect, embryos are screened to permit the identification of suitable mutant $p27^{Kip1}$ embryos for implantation to form transgenic animals. For example, one or more cells are removed from the pre-implantation embryo. When equal division of the embryo is used, the embryo is typically not cultivated past the morula stage (32 cells). Division of the pre-implantation embryo (reviewed by Williams et al., *Theriogenology* 22:521-31 (1986)) results in two "hemi-embryos" (hemi-morula or hemi-blastocyst), one of which is capable of subsequent development after implantation into the appropriate female to develop in utero to term. Although equal division of the pre-implantation embryo is typical, it is to be understood that such an embryo can be unequally divided either intentionally or unintentionally into two hemi-embryos. Essentially, one of the embryos which is not analyzed usually has a sufficient cell number to develop to full term in utero. In a specific embodiment, the hemi-embryo (which is not analyzed), if shown to be transgenic, can be used to generate a clonal population of transgenic animals, such as by embryo splitting.

One of the hemi-embryos formed by division of pre-implantation embryos can be analyzed to determine if the mutant $p27^{Kip1}$ gene has integrated into the genome of the organism. Each of the other hemi-embryos can be maintained for subsequent implantation into a recipient female, typically of the same species. A typical method for detecting a mutant $p27^{Kip1}$ gene at this early stage in the embryo's development uses these hemi-embryos in connection with allele-specific PCR, which can differentiate between a mutant $p27^{Kip1}$ gene and a wildtype $p27^{Kip1}$ gene. (See, e.g., McPherson et al. (eds) *PCR2: A Practical Approach*, Oxford University Press (1995); Cha et al., *PCR Methods Appl.* 2:14-20 (1992); the disclosures of which are incorporated by reference herein.)

After a hemi-embryo is identified as a transgenic hemi-embryo, it optionally can be cloned. Such embryo cloning can be performed by several different approaches. In one cloning method, the transgenic hemi-embryo can be cultured in the same or in a similar media as used to culture individual oocytes to the pre-implantation stage. The "transgenic embryo" so formed (typically a transgenic morula) can then be divided into "transgenic hemi-embryos" which can be implanted into a recipient female to form a clonal population of two transgenic non-human animals. Alternatively, the two transgenic hemi-embryos obtained can be again cultivated to the pre-implantation stage, divided, and recultivated to the transgenic embryo stage. This procedure can be repeated until the desired number of clonal transgenic embryos having the same genotype are obtained. Such transgenic embryos can then be implanted into recipient females to produce a clonal population of transgenic non-human animals.

In addition to the foregoing methods for detecting the presence of a mutant $p27^{Kip1}$ gene, other methods can be used. Such methods include, for example, in utero and post partum analysis of tissue. In utero analysis can be performed by several techniques. In one, transvaginal puncture of the amniotic cavity is performed under echoscopic guidance (see, e.g., Bowgso et al., *Bet. Res.* 96:124-27 (1975); Rumsey et al., *J. Anim. Sci.* 39:386-91 (1974)). This involves recovering amniotic fluid during gestation. Most of the cells in the amniotic fluid are dead. Such cells, however, contain genomic DNA which can be subjected to analysis (e.g., by PCR) for the mutant p27$^{Kip1}$ gene as an indication of a successful transgenesis. Alternatively, fetal cells can be recovered by chorion puncture. This method also can be performed transvaginally and under echoscopic guidance. In this method, a needle can be used to puncture the recipient animal's placenta, particularly the placentonal structures, which are fixed against the vaginal wall. Chorion cells, if necessary, can be separated from maternal tissue and subjected to PCR analysis for the mutant p27$^{Kip1}$ gene as an indication of successful transgenesis.

The presence of a mutant p27$^{Kip1}$ gene can also be detected after birth. In such cases, the presence of a mutant p27$^{Kip1}$ gene can be detected by taking an appropriate tissue biopsy, such as from an ear or tail of the putative transgenic animal. The presence of a mutant p27$^{Kip1}$ gene can also be detected by assaying for expression of the mutant p27$^{Kip1}$ polypeptide in a tissue.

The location and number of integration events can be determined by methods known to the skilled artisan. (See, e.g., Ausubel et al., supra; Sambrook et al., supra.) For example, PCR or Southern blot analysis of genomic DNA extracted from infected oocytes and/or the resulting embryos, offspring and tissues derived therefrom, can be employed when information concerning site of integration of the viral DNA into the host genome is desired. To examine the number of integration sites present in the host genome, the extracted genomic DNA can typically be digested with a restriction enzyme which cuts at least once within the vector sequences. If the enzyme chosen cuts twice within the vector sequences, a band of known (i.e., predictable) size is generated in addition to two fragments of novel length which can be detected using appropriate probes.

Other methods of preparing transgenic animals are disclosed, for example, in U.S. Pat. No. 5,633,076 or U.S. Pat. No. 6,080,912; and in International Patent Publications WO 97/47739, WO 99/37143, WO 00/75300, WO 00/56932, and WO 00/08132, the disclosures of which are incorporated herein by reference in their entirety.

EXAMPLES

The present invention can be illustrated by the following Examples. These examples illustrate principles of the present invention and are not intended to limit the scope of the invention.

Example 1

In this example, the effect of an amino acid substitution, threonine 187 to alanine in a mouse p27$^{Kip1}$ gene, on mice was studied.
Methods
Mice
To construct the genomic targeting vector, a 5.9 kilobase (kb) Bam HI fragment was isolated from a 17 kb Not I fragment which contains the entire coding region of the p27$^{Kip1}$ gene obtained from a mouse 129/Sv 1 genomic library (as described by Fero et al., *Cell* 85:733-44 (1996)). Codon 187 of exon 2, which encoded threonine, was mutated to alanine site directed mutagenesis (acg→gcg) to make the p27$^{T187A}$ allele. A 3 kb Sac I fragment containing an antibiotic resistance expression cassette (comprising a pgk promoter driving expression of a neomycin resistance gene followed by a transcription termination) was isolated as a Bam HI/Hind III fragment from pBS302 (Gibco BRL). Nucleic acids encoding loxP sequences were attached to each end of an antibiotic resistance expression cassette. The modified expression cassette was inserted into a Sac I site in the p27$^{Kip1}$ promoter of the 5.9 kb Bam HI p27$^{Kip1}$ gene fragment (in the antisense orientation) to create the construct p27T187A 5.9 Neo/STOP. This construct was then cloned into the pPNT vector (Fero et al., *Cell* 85:733-44 (1996)), thus creating the genomic targeting vector.

For construction of mouse embryonic stem cells containing the p27T187A 5.9 Neo/STOP construct, the targeting vector was linearized with Not I and transduced by electroporation into mouse XY AK7 embryonic stem (ES) cells (Friedrich et al., *Genes & Development* 5:1513-23 (1991)). Transduced embryonic stem cells were selected in 400 µg/ml G418 and 0.4 µM FIAU. Neomycin resistant colonies of ES cells were screened for homologous recombination of the p27T187A 5.9 Neo/STOP construct at the p27$^{Kip1}$ locus by Southern blotting using a probe external to the 5' end of the targeting construct. In all 5 ES cell clones used for blastocyst injection, integration of the T187A mutation was verified by DNA sequence analysis. Transduced ES cells containing the homologously integrated p27T187A 5.9 Neo/STOP were designated p27$^{T187A}$ ES cells.

p27$^{T187A}$ ES cells were introduced by microinjection into 5 dpc C57/B6J mouse embryos. Germline transmission of the p27T187A 5.9 Neo/STOP construct was identified in male chimeras representing three separate ES cell clones.

To excise the neo/STOP cassette from the p27$^{Kip1}$ gene, chimeric male mice were bred with female CMV-cre transgenic mice (TgN(CMV-Cre)1AN) (Nagy et al., *Curr. Biol.* 8:661-64 (1998)). Excision of the neo/STOP cassette was verified by PCR using primers derived from the p27$^{T187A}$ genomic sequence upstream of the Sac I site (Y1, GAGCAG-GTTTGTTG GCAGTCGTACACCTCC) (SEQ ID NO:1), from the neomycin gene (A4, CGTGGGATCATTGT TTTTCTCTTG) (SEQ ID NO:2), and from genomic sequence downstream of the Sac I site (H3, CCAATATG-GCGGTGGAAGGGAGGCTGA) (SEQ ID NO:3). Homozygous integration of the T187A mutation was confirmed by the presence of a 34 base pair (bp) loxP site insertion into the wildtype 0.25 kb PCR fragment using primers Y1 and H3.

Mouse Embryonic Fibroblasts p27$^{T187A}$ heterozygous males and females were crossed and embryos were dissected 12.5-13.5 days after detection of vaginal plugs. The head and internal organs were removed, and the embryos were minced and incubated in 0.05% trypsin for 5 minutes. The cells were resuspended in Dulbecco's modified Eagle medium (DMEM) supplemented with 10% FBS. After centrifugation, the supernatant was discarded, and the cell suspension from each embryo was cultivated on a 10-cm dish in 8 ml of DMEM with 10% FBS until confluency was reached. After this time, the cells were trypsinized, counted and plated at 1.4×10$^6$ cells/10-cm dish every three days.

Cell Culture

Passage 2-3 mouse embryonic fibroblasts (MEFs) were plated as 1.4×10$^6$ cells/10-cm dish grown in DMEM with 10% FBS for 3 days after which the media was removed, the plates washed with PBS, and the cells incubated in DMEM containing 0.1% FBS for 72 hours. The cells were then washed with PBS, trypsinized, counted and resuspended in DMEM containing 10% FBS at $1.4 \times 10^6$ cells/10-cm dish and $0.5 \times 10^5$ cells/6-cm dish. For each time point, the cells were labeled with 10 μM BrdU (Sigma) for 30 minutes, scraped off the plate, washed with PBS and fixed in 70% ethanol for at least 24 hours. Nuclei were purified and labeled with 100 μl anti BrdU-FITC antibody (Pharmingen) as previously described (White et al., *Cytometry* 11:314-17 (1990)). After this incubation nuclei were treated with RNAse A, counterstained with propidium iodide (100 μg/ml) and analyzed on a Becton Dickinson Flow Cytometer using Becton Dickinson Cell Quest software.

To separate G1 from S phase cells, cells were labeled with Hoechst Stain (Sigma) (10 μg/ml) for 30 minutes, trypsinized and separated on a Vantage SE flow cytometer (BD systems) using Cell Quest software. For $p27^{Kip1}$ half life measurements, cycloheximide (chx) (10 μg/ml final concentration) was added to the cells at the indicated times. $p27^{Kip1}$ protein levels were determined by immunoblotting. The resulting autoradiograms were scanned and the intensity of the $p27^{Kip1}$ bands quantitated using Image Quant software (Molecular Dynamics) and normalized to actin controls.

Isolation and Stimulation of T Lymphocytes

Splenic $CD4^+$ T cells were purified following red cell lysis (Whole Blood Erythrocyte Lysing Kit, R&D systems). Mononuclear cells were enriched using ficoll gradient centrifugation. $CD4^+$ T cells were isolated using the mouse T Cell CD4 Subset Columns (R&D Systems). $CD4^+$ T cells were activated with plate-bound anti-CD3 antibody without or with the addition of recombinant mouse IL2 (Pharmingen) (i.e., 0, 10 Units of IL-2/ml or 100 Units of IL-2/ml). 72 hours after stimulation T cells were labeled with [$^3$H] thymidine for 4 hours, harvested and the incorporation of radioactivity into DNA determined. All measurements were done in triplicate.

Immunoblotting

The antibodies used for immunoblotting were mouse monoclonal anti-$p27^{Kip1}$ (Transduction Laboratories), rabbit polyclonal anti-cyclin A (Santa Cruz Biotechnology), anti-Actin (Santa Cruz), and anti-Cdk2 (Santa Cruz).

Wound Healing

Full thickness punch wounds (4 mm) were applied as previously described (Subramaniam et al., *Amer. J. Path.* 150: 1701-09 (1997)). Animals were injected with BrdU (1 mg/ml, 30 μl/g) 16 hours before they were sacrificed. Wounds were excised, fixed and embedded in paraffin 4.5 days after wounding (Kyriakides et al., *J. Invest. Dermatol.* 113:782-87 (1999)). Wounds were stained with anti-BrdU Ab (AB1, Neo-Markers). BrdU staining was visualized using the Darko Ark Kit and counterstained with hematoxylin and eosin. Wound sizes and epithelial gap diameters were determined by optical micrometer measurements using 100× magnification.

Results

In this example, the role of T187 phosphorylation in determining $p27^{Kip1}$ protein abundance, and in controlling cell proliferation, was examined by examining wildtype mice (having unmutated $p27^{Kip1}$) and $p27^{T187A}$ mice. ($p27^{T187A}$ mice express a non-phosphorylatable form of $p27^{Kip1}$ in which the conserved threonine at position 187 was changed to alanine.) $p27^{T187A}$ mice were prepared by precisely replacing the wildtype $p27^{Kip1}$ gene with the $p27^{T187A}$ allele. Previous experiments using cultured fibroblasts had shown that ectopic over-expression of $p27^{T187A}$ imposed an irreversible G1 arrest (Sheaff et al., *Genes & Development* 11: 1464-78 (1997)). Thus, it was expected that over-expression of $p27^{T187A}$ in mice would also impose an irreversible G1 arrest on cells harboring this mutant allele. To prevent this G1 block to cell replication, a 'lox-STOP-lox' element was placed within the promoter of the $p27^{T187A}$ allele so that the mutant allele could be conditionally activated with the Cre recombinase.

Mice heterozygous for the $p27^{T187A}$ allele (containing the lox-STOP-lox construct) were bred to mice that constitutively express Cre recombinase in the germline, which resulted in deletion of the lox-STOP-lox element. The $p27^{T187A}$ (Δlox-STOP-lox) allele was bred to homozygosity and shown to express the $p27^{T187A}$ protein at levels equivalent to the wildtype allele in all tissues. Control experiments showed that $p27^{T187A}$ mice and wildtype $p27^{Kip1}$ mice were equally able to inhibit Cdk2 in vitro kinase activity when either histone H1 or the retinoblastoma protein was used as a substrate (Sheaff et al., *Genes & Development* 11:1464-78 (1997)). Therefore, the T187A substitution did not produce an intrinsic change in its molecular properties as a Cdk inhibitor. Surprisingly, expression of the $p27^{T187A}$ allele did not affect viability or fertility, and thus did not produce the expected block in G1 replication. Consequently, all further experiments were performed on mice homozygous for the $p27^{T187A}$ allele, and which did not contain the Cre recombinase transgene.

The effect of the T187A amino acid substitution on regulation of the $p27^{Kip1}$ protein was determined by comparing the protein levels of p27 and $p27^{T187A}$ in mouse embryonic fibroblasts (MEFs) that were made quiescent by serum deprivation and then stimulated to synchronously enter the cell cycle by readdition of serum. The half lives of p27 and $p27^{T187A}$ were measured in G0, G1 and S phase MEFs. Cells were synchronized by serum starvation (G0) and refeeding (G1=12 hours post refeeding, S=24 hours post refeeding). p27 protein levels were determined by immunoblotting of cell extracts from cells synchronized through two cell cycles. Control MEFs were synchronized by serum starvation and then stimulated to enter the cell cycle by refeeding with serum. One group of cells was allowed to proceed through G1, while the other group was treated with the proteasome inhibitor MG-132 (10 μM) at 6 hours post serum stimulation. p27 protein levels were then measured at the indicated time points by immunoblotting. Quiescent Skp2+/+ and skp2 −/− MEFs were stimulated to re-enter the cell cycle by addition of serum, and p27 protein levels were determined at the indicated time points by immunoblotting.

In control MEFs, p27 protein levels declined to low levels between 12 and 15 hours after serum stimulation. This time corresponded to the early/mid-G1 part of the cell cycle. p27 protein levels remained at low levels for the duration of the cell cycle. $p27^{T187A}$ was expressed at the same level as wildtype p27 in quiescent MEFs. This observation is consistent with the observation that p27 and $p27^{T187A}$ were expressed at equal levels in mouse tissues in vivo (and which are composed largely of non-dividing cells). Serum stimulation of MEF's containing $p27^{T187A}$ caused the $p27^{T187A}$ protein levels to decline with kinetics similar to those of wildtype p27. However, in contrast to the wildtype protein, $p27^{T187A}$ protein then re-accumulated as cells completed G1 and entered S phase. Indeed, in late S/G2 the amount of $p27^{T187A}$ rose to a level that was similar to its abundance in quiescent cells. This increase in abundance was associated with an increased amount of p27 bound to cyclin A and a 50% reduction in cyclin A-associated kinase activity. There was no change in total cyclin A protein levels, and the length of S phase was not altered. These studies demonstrated that p27 was down-regulated in a T187-dependent manner in S and G2, and independently of T187 in G1.

The absence of the T187-dependent pathway for p27 turnover had significant effects on cell proliferation in various cells and tissues of the p27$^{T187A}$ mouse. In general, rising levels of p27$^{T187A}$, which occurred in late G1/S/G2 cells, created a barrier to cell cycle progression. The severity of the ensuing proliferation defect varied among different cell types, however. A modest effect was seen in MEFs, where expression of p27$^{T187A}$ caused a 20-30% reduction in the number of cells which entered S phase after serum stimulation. This result was later confirmed using three independently isolated MEF strains from three different founder mice.

A relatively greater defect was seen when purified CD4$^+$ splenic T lymphocytes were stimulated to proliferate with antibodies directed against the T cell antigen receptor. DNA replication was reduced by 80% in cells expressing p27$^{T187A}$ compared to control T cells. Addition of exogenous IL-2 partially restored proliferation of the cells expressing p27$^{T187A}$, suggesting that high levels of IL-2 might promote a T187 independent pathway for decreasing p27.

A defect in cell proliferation was also observed in dermal keratinocytes expressing p27$^{T187A}$. Keratinocyte proliferation was induced in vivo by creating circular, 4 mm full thickness punch wounds in the skin overlying the scapula and extending through the epidermis and dermis. The rate of healing was monitored by gross inspection and by histological examination at 4.5 days after wounding. This analysis revealed a delay in wound re-epithelialisation in the p27$^{T187A}$ mice. The epithelial gap measured as the distance between the keratinocyte edges growing into the woundbed made up 60% (±5) of the entire wound in the P27$^{T187A}$ mice as compared to 35% (±9) in the control mice (n=12). This difference was most likely a result of an impaired proliferative response, because p27$^{T187A}$ keratinocytes at the wound edge displayed reduced levels of BrdU incorporation (13.5% (±8.5) p27$^{187A}$ versus 35% (±5) control). No difference was observed in the healing of incisional wounds in p27$^{T187A}$ versus control mice, which occurs mostly by epithelial cell migration rather than proliferation.

Surprisingly, despite the restraint on cell proliferation created by the p27$^{T187A}$ mutant protein, mice expressing this protein developed normally and attained an average size that was even larger than wildtype mice. Growth curves for female p27$^{Kip1}$ +/+, p27 −/− (homozygous null alleles) and p27$^{T187A}$/p27$^{T187A}$ mice were prepared. An average of 30 mice was observed of each type. The p27$^{Kip1}$ +/+ and p27$^{T187A}$/p27$^{T187A}$ mice were littermates (F2 hybrids B6/C57×129/Sv). Weight data for the p27 null mice were obtained from an earlier study, which used mice of the same genetic background as those used here (Fero et al., Cell 85:733-44 (1996)).

One possibility was that the T187A substitution had partially disabled p27$^{Kip1}$ function, resulting in cellular hyperplasia similar to that seen in the p27$^{Kip1}$ knockout mouse. This possibility was examined in the thymus of the p27$^{T187A}$ mice, which like all other organs was enlarged in proportion to overall body size. In contrast to the results observed in p27$^{Kip1}$ knockout mice (Fero et al., Nature 396:177-80 (1998); Nakayama et al., Cell 85:707-20 (1996); Kiyokawa et al., Cell 85:721-32 (1996)), mice expressing p27$^{T187A}$ did not show an increased amount of cell proliferation, as determined by BrdU labeling. This result indicates that the T187A substitution and the p27$^{Kip1}$ gene deletion affected organ size by different mechanisms. Further, other phenotypes associated with p27$^{Kip1}$ deficiency were not seen in the mice expressing p27$^{T187A}$, including female sterility, pituitary tumorigenesis, and disrupted retinal architecture.

These results showed that p27$^{Kip1}$ abundance is controlled by two different mechanisms, the first acting in early/mid G1 cells and the second in late G1, S and G2. The increased turnover of p27$^{Kip1}$ protein was the mechanism underlying not only the T187 pathway for p27$^{Kip1}$ regulation, but the earlier G1 pathway as well. In quiescent cells, p27$^{Kip1}$ was relatively stable with a half life of 10-12 hours. Serum stimulation decreased p27$^{Kip1}$ stability, reducing its half life to approximately 2 hours in both G1 and S phase cells. p27$^{T187A}$ was also stable in quiescent cells, and after serum stimulation became unstable in mid-G1 similar to the wildtype protein. In S phase cells, however, p27$^{T187A}$ became stable again, acquiring a long half life very similar to what it had been in quiescent, mitogen starved cells. Thus, rapid turnover of p27$^{Kip1}$ in S phase cells requires T187, whereas the rapid turnover of p27$^{Kip1}$ in G1 cells does not. These results also implied that the proteolytic pathway which degraded p27$^{Kip1}$ in G1 cells was not operative in S phase.

This G1-specific turnover pathway for p27$^{Kip1}$ is not a unique feature of cells as they exit quiescence, but rather occurs during each mitotic cycle. Quiescent MEFs were stimulated with serum mitogens for 18 hours at which time they were separated by flow cytometry into G1 and S phase populations. As seen previously, p27$^{Kip1}$ protein levels were lower in G1 cells than in quiescent cells. In the S phase population, however, the abundance of wildtype p27$^{Kip1}$ declined further whereas the opposite occurred in MEFs expressing p27$^{T187A}$ polypeptide. The S phase cells were then replated and allowed to progress through the division cycle until a time when 80% of the cells had entered the next G1 phase. The abundance of p27$^{T187A}$ declined again in the second G1 just as it had in the first G1, demonstrating the periodic nature of the G1-turnover pathway.

Phosphorylation of p27$^{Kip1}$ on T187 is known to trigger its ubiquitination by the Skp2-containing SCF E3 complex, and its subsequent turnover in the proteasome (Sheaff et al., Genes & Development 11:1464-78 (1997); Vlach et al., EMBO J. 15:6595-604 (1996); Muller et al., Oncogene 15:2561-76 (1997); Sutterluty et al., Nature Cell Biol. 1:207-14 (1999); Rolfe et al., J. Mol. Med. 75:5-17 (1997); Carrano et al., Nature Cell Biol. 1:193-99 (1999); Tsvetkov et al., Curr. Biol. 9:661-64 (1999)). The turnover of p27$^{Kip1}$ in G1 cells was also proteosome and Skp2-dependent. Quiescent, serum starved MEFs were re-stimulated with serum and six hours later treated with MG132, an inhibitor of proteasomal proteolysis. This prevented the normal decrease in p27$^{Kip1}$ protein levels that occurs in mid-G1. Furthermore, p27$^{Kip1}$ protein levels did not decline, either in G1 or in S phase, in serum stimulated skp2 null MEFs. These cells presumably continue to proliferate because Skp2 is also needed for degradation of cyclin E31. Therefore, although the trigger for p27$^{Kip1}$ turnover is different in G1 versus S phase, both pathways ultimately lead to the degradation of p27$^{Kip1}$ by Skp2- and proteosome-dependent mechanisms.

These data show that T187-dependent turnover of p27$^{Kip1}$ is important for normal regulation of p27$^{Kip1}$ and normal control of cell division. However, contrary to the expected results, inactivating this pathway has neither a universal nor severe effect on cell proliferation. This observation is explained, at least in part, by a previously unrecognized T187-independent pathway for p27$^{Kip1}$ degradation that is activated during each G1 phase of the cell cycle. This pathway allows many cells expressing p27$^{T187A}$ to complete the cell cycle before the re-accumulation of p27$^{Kip1}$ in S phase can stop it. The T187 pathway, by keeping p27$^{Kip1}$ levels low for the duration of S and G2, allows the cell to slow its rate of progression through this part of the cell cycle (for instance, in response to DNA damage) without having to confront the rising p27$^{Kip1}$ levels which would otherwise occur.

Thus, two proteolytic pathways act in sequence during the cell cycle to control p27$^{Kip1}$ abundance. The first pathway functions during early to mid G1 and is triggered by mitogens. It may be activated by Ras and Myc, and underlie the ability of these proteins to reduce p27$^{Kip1}$ abundance and promote serum-independent entry into S phase (Leone et al., *Nature* 387:422-26 (1997); O'Hagan et al., *Genes & Development* 14:2185-91 (2000)). Inhibition of p27$^{Kip1}$ at the level of translation (Agrawal et al., *Mol. Cell. Biol.* 16:4327-36 (1996); Hengst et al., *Science* 271:1861-64 (1996); Millard et al., *Mol. Cell. Biol.* 20:5947-59 (2000); Millard et al., *J. Biol. Chem.* 272:7093-98 (1997)), and by sequestration into cyclin D/Cdk complexes (Sherr et al., *Genes & Development* 13:1501-12 (1999)) also contribute to down regulation of p27$^{Kip1}$ during the early to mid G1 cell cycle period. Down-regulation of p27$^{Kip1}$ by the concerted action of these pathways results in the initial production of active cyclin E-Cdk2, and consequently the onset of the second pathway for p27$^{Kip1}$ turnover. This second pathway operates in late G1, S and G2, and is dependent upon Cdk2-mediated phosphorylation of p27$^{Kip1}$ on T187. Once initiated, this second pathway would be amplified by a self-reinforcing positive feedback loop, and therefore would continue even if the initial mitogenic stimulus were withdrawn. In this way, inactivation of P$_{27}^{Kip1}$ switches in mid G1 from being mitogen-dependent to being mitogen-independent, which is analogous to the consecutive mitogen-dependent and mitogen-independent pathways that inactivate Rb during the same cell cycle interval (Hatakeyama et al., *Cold Spring Harbor Symposia on Quantitative Biology* 59:1-10 (1994)). Sequentially acting pathways that inactivate key cell cycle inhibitors can be the biochemical underpinnings of the cell cycle transition from mitogen-dependence to mitogen-independence, which has been called the G1 restriction point (Pardee, *Proc. Natl. Acad. Sci. USA* 71:1286-90 (1974)).

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

What is claimed is:

1. An isolated transgenic somatic or embryonic stem cell having a mutant p27$^{Kip1}$ gene lacking a Cdk2 phosphorylation site integrated at the endogenous p27$^{Kip1}$ gene such that there is a loss of endogenous wildtype p27$^{Kip1}$ activity, wherein the mutant p27$^{Kip1}$ gene encodes a mutant p27$^{Kip1}$ polypeptide having a longer half-life in S phase than wildtype p27$^{Kip1}$ polypeptide.

2. The transgenic cell of claim 1, wherein the mutant p27$^{Kip1}$ polypeptide inhibits Cdk2 in vitro kinase activity.

3. The transgenic cell of claim 1, wherein the mutant p27$^{Kip1}$ polypeptide is p27$^{T187A}$.

4. An isolated transgenic mouse cell having a mutant p27$^{Kip1}$ gene lacking a Cdk2 phosphorylation site integrated at the endogenous p27$^{Kip1}$ gene such that there is a loss of endogenous wildtype p27$^{Kip1}$ activity, wherein the mutant p27$^{Kip1}$ gene encodes a mutant p27Kip1 polypeptide having a longer half-life in S phase than wild-type p27$^{Kip1}$1 polypeptide.

5. The isolated transgenic mouse cell of claim 4, wherein the cell is a somatic cell, a germ cell, a fertilized egg, or an embryonic stem cell.

6. The isolated transgenic mouse cell of claim 5, wherein the germ cell is a an oocyte, primordial germ cell, sperm cell, or spermatocyte.

* * * * *